(12) United States Patent
Davis et al.

(10) Patent No.: US 7,063,840 B2
(45) Date of Patent: Jun. 20, 2006

(54) TIE-2 LIGANDS, METHODS OF MAKING AND USES THEREOF

(75) Inventors: Samuel Davis, New York, NY (US); Joanne Bruno, Bloomingdale, NJ (US); Mitchell Goldfarb, River Edge, NJ (US); Thomas H. Aldrich, Ossining, NY (US); Peter C. Maisonpierre, Croton, NY (US); Czeslaw Radziejewski, Somers, NY (US); Pamela F. Jones, Leeds (GB); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 584 days.

(21) Appl. No.: 10/179,615

(22) Filed: Jun. 24, 2002

(65) Prior Publication Data

US 2003/0166857 A1 Sep. 4, 2003

Related U.S. Application Data

(60) Division of application No. 08/817,318, filed on Sep. 16, 1999, which is a continuation-in-part of application No. 08/373,579, filed on Jan. 17, 1995, now Pat. No. 6,650,490, which is a continuation-in-part of application No. 08/348,492, filed on Dec. 2, 1994, now Pat. No. 5,879,672, which is a continuation-in-part of application No. 08/330,261, filed on Oct. 27, 1994, now Pat. No. 5,521,073, and application No. 08/319,932, Oct. 7, 1994, now Pat. No. 5,643,755, application No. 08/353,503, filed on Dec. 9, 1994, now abandoned.

(51) Int. Cl.
*C07K 16/24* (2006.01)
*A61K 39/395* (2006.01)

(52) U.S. Cl. ............... 424/139.1; 424/141.1; 424/145.1; 424/178.1; 530/387.1; 530/388.1; 530/387.3; 530/388.23; 530/389.2

(58) Field of Classification Search ............ 424/139.1, 424/141.1, 145.1, 178.1; 530/387.1, 388.1, 530/387.3, 388.23, 389.2
See application file for complete search history.

(56) References Cited

U.S. PATENT DOCUMENTS 4,054,646 A * 10/1977 Giaever .................... 435/5

FOREIGN PATENT DOCUMENTS

WO     WO 94/11499     5/1994

OTHER PUBLICATIONS

BLOOD, vol. 80, No. 10, issued Nov. 15, 1992, Korhonen et al., "Enhanced Expression of the *tie* Receptor Tyrosine Kinase in Endothelial Cells During Neovascularization", pp. 2548-2555.
Molecular and Cellular Biology, vol. 12, No. 14, issued Apr. 1992, Partanen et al., "A Novel Endothelial Cell Surface Receptor Tyrosine Kinase with Extracellular Epidermal Growth Factor Homology Domains", pp. 1698-1707.
NATURE, vol. 376, No. 6, issued Jul. 6, 1995, Sato et al., "Distinct roles of the receptor tyrosine kinases Tie-1 and Tie-2 in blood vessel formation", pp. 70-74.
ONCOGENE, vol. 8, 1993, Dumont et al., "The endothelial-specific receptor tyrosine kinase, tek, is a member of a new subfamily of receptors", pp. 1293-1301.
ONCOGENE, vol. 8, 1993, Maisonpierre et al., "Distinct rat genes with related profiles of expression define TIE receptor tyrosine kinase family", pp. 1631-1637.
Proc. Natl. Acad. Sci., vol. 87, issued Nov. 1990, Partanen et al., "Putative tyrosine kinases expressed in K562 human leukemia cells", pp. 8913-8917.
Proc. Natl. Acad. Sci., vol. 90, issued Oct. 1993, Sato, et al., "tie-1 and tie-2 define another class of putative receptor tyrosine kinase genes expressed in early embryonic vascular system", pp. 9355-9358.

* cited by examiner

*Primary Examiner*—Prema Mertz
(74) *Attorney, Agent, or Firm*—Valeta Gregg, Esq.

(57) ABSTRACT

The present invention provides for an isolated nucleic acid molecule encoding a human TIE-2 ligand. In addition, the invention provides for a receptor body which specifically binds a human TIE-2 ligand. The invention also provides an antibody which specifically binds a human TIE-2 ligand. The invention further provides for an antagonist of human TIE-2. The invention also provides for therapeutic compositions as well as a method of blocking blood vessel growth, a method of promoting neovascularization, a method of promoting the growth or differentiation of a cell expressing the TIE-2 receptor, a method of blocking the growth or differentiation of a cell expressing the TIE-2 receptor and a method of attenuating or preventing tumor growth in a human.

11 Claims, 19 Drawing Sheets

Fig. 4A

```
            10        20        30        40        50        60        70        80
             .         .         .         .         .         .         .         .
CAGCTGACTCAGGCAGGCTCCATGCTGAACGGTCACACAGAGAGGAAACAATAAATCTCAGCTACTATGCAATAAATATC 90       100       110       120       130       140       150       160
             .         .         .         .         .         .         .         .
TCAAGTTTTAACGAAGAAAAACATCATTGCAGTGAAATAAAAAATTTTAAAATTTTAGAACAAAGCTAACAAATGGCTAG 170       180       190       200       210       220       230       240
             .         .         .         .         .         .         .         .
TTTTCTATGATTCTTCTTCAAACGCTTTCTTTGAGGGGGAAAGAGTCAAACAAACAAGCAGTTTTACCTGAAATAAAGAA 250       260       270       280       290       300       310
             .         .         .         .         .         .         .
CTAGTTTTAGAGGTCAGAAGAAAGGAGCAAGTTTTGCGAGAGGCACGGAAGGAGTGTGCTGGCAGTACA ATG ACA
                                                                        M   T>

320           330           340           350           360           370
            .             .             .             .             .             .
GTT TTC CTT TCC TTT GCT TTC CTC GCT GCC ATT CTG ACT CAC ATA GGG TGC AGC AAT CAG
 V   F   L   S   F   A   F   L   A   A   I   L   T   H   I   G   C   S   N   Q>

380           390           400           410           420           430
            .             .             .             .             .             .
CGC CGA AGT CCA GAA AAC AGT GGG AGA AGA TAT AAC CGG ATT CAA CAT GGG CAA TGT GCC
 R   R   S   P   E   N   S   G   R   R   Y   N   R   I   Q   H   G   Q   C   A>

440           450           460           470           480           490
            .             .             .             .             .             .
TAC ACT TTC ATT CTT CCA GAA CAC GAT GGC AAC TGT CGT GAG AGT ACC ACA GAC CAG TAC
 Y   T   F   I   L   P   E   H   D   G   N   C   R   E   S   T   T   D   Q   Y>

500           510           520           530           540           550
            .             .             .             .             .             .
AAC ACA AAC GCT CTG CAG AGA GAT GCT CCA CAC GTG GAA CCG GAT TTC TCT TCC CAG AAA
 N   T   N   A   L   Q   R   D   A   P   H   V   E   P   D   F   S   S   Q   K>

560           570           580           590           600           610
            .             .             .             .             .             .
CTT CAA CAT CTG GAA CAT GTG ATG GAA AAT TAT ACT CAG TGG CTG CAA AAA CTT GAG AAT
 L   Q   H   L   E   H   V   M   E   N   Y   T   Q   W   L   Q   K   L   E   N>
```

Fig. 4B

```
      620         630         640         650         660         670
       •           •           •           •           •           •
TAC ATT GTG GAA AAC ATG AAG TCG GAG ATG GCC CAG ATA CAG CAG AAT GCA GTT CAG AAC
 Y   I   V   E   N   M   K   S   E   M   A   Q   I   Q   Q   N   A   V   Q   N>

680         690         700         710         720         730
       •           •           •           •           •           •
CAC ACG GCT ACC ATG CTG GAG ATA GGA ACC AGC CTC CTC TCT CAG ACT GCA GAG CAG ACC
 H   T   A   T   M   L   E   I   G   T   S   L   L   S   Q   T   A   E   Q   T>

740         750         760         770         780         790
       •           •           •           •           •           •
AGA AAG CTG ACA GAT GTT GAG ACC CAG GTA CTA AAT CAA ACT TCT CGA CTT GAG ATA CAG
 R   K   L   T   D   V   E   T   Q   V   L   N   Q   T   S   R   L   E   I   Q>

800         810         820         830         840         850
       •           •           •           •           •           •
CTG CTG GAG AAT TCA TTA TCC ACC TAC AAG CTA GAG AAG CAA CTT CTT CAA CAG ACA AAT
 L   L   E   N   S   L   S   T   Y   K   L   E   K   Q   L   L   Q   Q   T   N>

860         870         880         890         900         910
       •           •           •           •           •           •
GAA ATC TTG AAG ATC CAT GAA AAA AAC AGT TTA TTA GAA CAT AAA ATC TTA GAA ATG GAA
 E   I   L   K   I   H   E   K   N   S   L   L   E   H   K   I   L   E   M   E>

920         930         940         950         960         970
       •           •           •           •           •           •
GGA AAA CAC AAG GAA GAG TTG GAC ACC TTA AAG GAA GAG AAA GAG AAC CTT CAA GGC TTG
 G   K   H   K   E   E   L   D   T   L   K   E   E   K   E   N   L   Q   G   L>

980         990         1000        1010        1020        1030
       •           •           •           •           •           •
GTT ACT CGT CAA ACA TAT ATA ATC CAG GAG CTG GAA AAG CAA TTA AAC AGA GCT ACC ACC
 V   T   R   Q   T   Y   I   I   Q   E   L   E   K   Q   L   N   R   A   T   T>

1040        1050        1060        1070        1080        1090
       •           •           •           •           •           •
AAC AAC AGT GTC CTT CAG AAG CAG CAA CTG GAG CTG ATG GAC ACA GTC CAC AAC CTT GTC
 N   N   S   V   L   Q   K   Q   Q   L   E   L   M   D   T   V   H   N   L   V>
```

Fig. 4C

```
     1100           1110           1120           1130           1140           1150
      .              .              .              .              .              .
AAT CTT TGC ACT AAA GAA GGT GTT TTA CTA AAG GGA GGA AAA AGA GAG GAA GAG AAA CCA
 N   L   C   T   K   E   G   V   L   L   K   G   G   K   R   E   E   E   K   P>

1160           1170           1180           1190           1200           1210
      .              .              .              .              .              .
TTT AGA GAC TGT GCA GAT GTA TAT CAA GCT GGT TTT AAT AAA AGT GGA ATC TAC ACT ATT
 F   R   D   C   A   D   V   Y   Q   A   G   F   N   K   S   G   I   Y   T   I>

1220           1230           1240           1250           1260           1270
      .              .              .              .              .              .
TAT ATT AAT AAT ATG CCA GAA CCC AAA AAG GTG TTT TGC AAT ATG GAT GTC AAT GGG GGA
 Y   I   N   N   M   P   E   P   K   K   V   F   C   N   M   D   V   N   G   G>

1280           1290           1300           1310           1320           1330
      .              .              .              .              .              .
GGT TGG ACT GTA ATA CAA CAT CGT GAA GAT GGA AGT CTA GAT TTC CAA AGA GGC TGG AAG
 G   W   T   V   I   Q   H   R   E   D   G   S   L   D   F   Q   R   G   W   K>

1340           1350           1360           1370           1380           1390
      .              .              .              .              .              .
GAA TAT AAA ATG GGT TTT GGA AAT CCC TCC GGT GAA TAT TGG CTG GGG AAT GAG TTT ATT
 E   Y   K   M   G   F   G   N   P   S   G   E   Y   W   L   G   N   E   F   I>

1400           1410           1420           1430           1440           1450
      .              .              .              .              .              .
TTT GCC ATT ACC AGT CAG AGG CAG TAC ATG CTA AGA ATT GAG TTA ATG GAC TGG GAA GGG
 F   A   I   T   S   Q   R   Q   Y   M   L   R   I   E   L   M   D   W   E   G>

1460           1470           1480           1490           1500           1510
      .              .              .              .              .              .
AAC CGA GCC TAT TCA CAG TAT GAC AGA TTC CAC ATA GGA AAT GAA AAG CAA AAC TAT AGG
 N   R   A   Y   S   Q   Y   D   R   F   H   I   G   N   E   K   Q   N   Y   R>

1520           1530           1540           1550           1560           1570
      .              .              .              .              .              .
TTG TAT TTA AAA GGT CAC ACT GGG ACA GCA GGA AAA CAG AGC AGC CTG ATC TTA CAC GGT
 L   Y   L   K   G   H   T   G   T   A   G   K   Q   S   S   L   I   L   H   G>
```

Fig. 4D

```
      1580            1590           1600           1610           1620           1630
       •               •              •              •              •              •
GCT GAT TTC AGC ACT AAA GAT GCT GAT AAT GAC AAC TGT ATG TGC AAA TGT GCC CTC ATG
 A   D   F   S   T   K   D   A   D   N   D   N   C   M   C   K   C   A   L   M>

1640            1650           1660           1670           1680           1690
       •               •              •              •              •              •
TTA ACA GGA GGA TGG TGG TTT GAT GCT TGT GGC CCC TCC AAT CTA AAT GGA ATG TTC TAT
 L   T   G   G   W   W   F   D   A   C   G   P   S   N   L   N   G   M   F   Y>

1700            1710           1720           1730           1740           1750
       •               •              •              •              •              •
ACT GCG GGA CAA AAC CAT GGA AAA CTG AAT GGG ATA AAG TGG CAC TAC TTC AAA GGG CCC
 T   A   G   Q   N   H   G   K   L   N   G   I   K   W   H   Y   F   K   G   P>

1760            1770           1780           1790           1800           1810
       •               •              •              •              •              •
AGT TAC TCC TTA CGT TCC ACA ACT ATG ATG ATT CGA CCT TTA GAT TTT TGA AAG CGCAATGT
 S   Y   S   L   R   S   T   T   M   M   I   R   P   L   D   F   *

1820      1830      1840      1850      1860      1870      1880      1890
  •         •         •         •         •         •         •         •
CAGAAGCGATTATGAAAGCAACAAAGAAATCCGGAGAAGCTGCCAGGTGAGAAACTGTTTGAAAACTTCAGAAGCAAACA 1900      1910      1920      1930      1940      1950      1960      1970
  •         •         •         •         •         •         •         •
ATATTGTCTCCCTTCCAGCAATAAGTGGTAGTTATGTGAAGTCACCAAGGTTCTTGACCGTCAATCTGGAGCCGTTTGAG 1980      1990      2000      2010      2020      2030      2040      2050
  •         •         •         •         •         •         •         •
TTCACAAGAGTCTCTACTTGGGGTGACAGTGCTCACGTGGCTCGACTATAGAAAACTCCACTGACTGTCGGGCTTTAAAA 2060      2070      2080      2090      2100      2110      2120      2130
  •         •         •         •         •         •         •         •
AGGGAAGAAACTGCTGAGCTTGCTGTGCTTCAAACTACTACTGGACCTTATTTTGGAACTATGGTAGCCAGATGATAAAT

2140
  •
ATGGTTAATTTC
```

Fig. 5A

```
          10        20        30        40        50        60        70        80
           .         .         .         .         .         .         .         .
CAGCTGACTCAGGCAGGCTCCATGCTGAACGGTCACACAGAGAGGAAACAATAAATCTCAGCTACTATGCAATAAATATC 90       100       110       120       130       140       150       160
           .         .         .         .         .         .         .         .
TCAAGTTTTAACGAAGAAAAACATCATTGCAGTGAAATAAAAAATTTTAAAATTTTAGAACAAAGCTAACAAATGGCTAG 170       180       190       200       210       220       230       240
           .         .         .         .         .         .         .         .
TTTTCTATGATTCTTCTTCAAACGCTTTCTTTGAGGGGGAAAGAGTCAAACAAACAAGCAGTTTTACCTGAAATAAAGAA 250       260       270       280       290       300       310
           .         .         .         .         .         .         .
CTAGTTTTAGAGGTCAGAAGAAAGGAGCAAGTTTTGCGAGAGGCACGGAAGGAGTGTGCTGGCAGTACA ATG ACA
                                                                       M   T>

320             330             340             350             360             370
         .               .               .               .               .               .
GTT TTC CTT TCC TTT GCT TTC CTC GCT GCC ATT CTG ACT CAC ATA GGG TGC AGC AAT CAG
 V   F   L   S   F   A   F   L   A   A   I   L   T   H   I   G   C   S   N   Q>

380             390             400             410             420             430
         .               .               .               .               .               .
CGC CGA AGT CCA GAA AAC AGT GGG AGA AGA TAT AAC CGG ATT CAA CAT GGG CAA TGT GCC
 R   R   S   P   E   N   S   G   R   R   Y   N   R   I   Q   H   G   Q   C   A>

440             450             460             470             480             490
         .               .               .               .               .               .
TAC ACT TTC ATT CTT CCA GAA CAC GAT GGC AAC TGT CGT GAG AGT ACG ACA GAC CAG TAC
 Y   T   F   I   L   P   E   H   D   G   N   C   R   E   S   T   T   D   Q   Y>

500             510             520             530             540             550
         .               .               .               .               .               .
AAC ACA AAC GCT CTG CAG AGA GAT GCT CCA CAC GTG GAA CCG GAT TTC TCT TCC CAG AAA
 N   T   N   A   L   Q   R   D   A   P   H   V   E   P   D   F   S   S   Q   K>

560             570             580             590             600             610
         .               .               .               .               .               .
CTT CAA CAT CTG GAA CAT GTG ATG GAA AAT TAT ACT CAG TGG CTG CAA AAA CTT GAG AAT
 L   Q   H   L   E   H   V   M   E   N   Y   T   Q   W   L   Q   K   L   E   N>
```

Fig. 5B

```
        620           630           640           650           660           670
         .             .             .             .             .             .
TAC ATT GTG GAA AAC ATG AAG TCG GAG ATG GCC CAG ATA CAG CAG AAT GCA GTT CAG AAC
 Y   I   V   E   N   M   K   S   E   M   A   Q   I   Q   Q   N   A   V   Q   N>

680           690           700           710           720           730
         .             .             .             .             .             .
CAC ACG GCT ACC ATG CTG GAG ATA GGA ACC AGC CTC CTC TCT CAG ACT GCA GAG CAG ACC
 H   T   A   T   M   L   E   I   G   T   S   L   L   S   Q   T   A   E   Q   T>

740           750           760           770           780           790
         .             .             .             .             .             .
AGA AAG CTG ACA GAT GTT GAG ACC CAG GTA CTA AAT CAA ACT TCT CGA CTT GAG ATA CAG
 R   K   L   T   D   V   E   T   Q   V   L   N   Q   T   S   R   L   E   I   Q>

800           810           820           830           840           850
         .             .             .             .             .             .
CTG CTG GAG AAT TCA TTA TCC ACC TAC AAG CTA GAG AAG CAA CTT CTT CAA CAG ACA AAT
 L   L   E   N   S   L   S   T   Y   K   L   E   K   Q   L   L   Q   Q   T   N>

860           870           880           890           900           910
         .             .             .             .             .             .
GAA ATC TTG AAG ATC CAT GAA AAA AAC AGT TTA TTA GAA CAT AAA ATC TTA GAA ATG GAA
 E   I   L   K   I   H   E   K   N   S   L   L   E   H   K   I   L   E   M   E>

920           930           940           950           960           970
         .             .             .             .             .             .
GGA AAA CAC AAG GAA GAG TTG GAC ACC TTA AAG GAA CAG AAA GAG AAC CTT CAA GGC TTG
 G   K   H   K   E   E   L   D   T   L   K   E   Q   K   E   N   L   Q   G   L>

980           990          1000          1010          1020          1030
         .             .             .             .             .             .
GTT ACT CGT CAA ACA TAT ATA ATC CAG GAG CTG GAA AAG CAA TTA AAC AGA GCT ACC ACC
 V   T   R   Q   T   Y   I   I   Q   E   L   E   K   Q   L   N   R   A   T   T>

1040          1050          1060          1070          1080          1090
         .             .             .             .             .             .
AAC AAC AGT GTC CTT CAG AAG CAG CAA CTC GAG CTG ATG GAC ACA GTC CAC AAC CTT GTC
 N   N   S   V   L   Q   K   Q   Q   L   E   L   M   D   T   V   H   N   L   V>
```

Fig. 5C

```
        1100          1110          1120          1130          1140          1150
         •             •             •             •             •             •
AAT CTT TGC ACT AAA GAA GTT TTA CTA AAG GGA GGA AAA AGA GAG GAA GAG AAA CCA TTT
 N   L   C   T   K   E   V   L   L   K   G   G   K   R   E   E   E   K   P   F>

1160          1170          1180          1190          1200          1210
         •             •             •             •             •             •
AGA GAC TGT GCA GAT GTA TAT CAA GCT GGT TTT AAT AAA AGT GGA ATC TAC ACT ATT TAT
 R   D   C   A   D   V   Y   Q   A   G   F   N   K   S   G   I   Y   T   I   Y>

1220          1230          1240          1250          1260          1270
         •             •             •             •             •             •
ATT AAT AAT ATG CCA GAA CCC AAA AAG GTG TTT TGC AAT ATG GAT GTC AAT GGG GGA GGT
 I   N   N   M   P   E   P   K   K   V   F   C   N   M   D   V   N   G   G   G>

1280          1290          1300          1310          1320          1330
         •             •             •             •             •             •
TGG ACT GTA ATA CAA CAT CGT GAA GAT GGA AGT CTA GAT TTC CAA AGA GGC TGG AAG GAA
 W   T   V   I   Q   H   R   E   D   G   S   L   D   F   Q   R   G   W   K   E>

1340          1350          1360          1370          1380          1390
         •             •             •             •             •             •
TAT AAA ATG GGT TTT GGA AAT CCC TCC GGT GAA TAT TGG CTG GGG AAT GAG TTT ATT TTT
 Y   K   M   G   F   G   N   P   S   G   E   Y   W   L   G   N   E   F   I   F>

1400          1410          1420          1430          1440          1450
         •             •             •             •             •             •
GCC ATT ACC AGT CAG AGG CAG TAC ATG CTA AGA ATT GAG TTA ATG GAC TGG GAA GGG AAC
 A   I   T   S   Q   R   Q   Y   M   L   R   I   E   L   M   D   W   E   G   N>

1460          1470          1480          1490          1500          1510
         •             •             •             •             •             •
CGA GCC TAT TCA CAG TAT GAC AGA TTC CAC ATA GGA AAT GAA AAG CAA AAC TAT AGG TTG
 R   A   Y   S   Q   Y   D   R   F   H   I   G   N   E   K   Q   N   Y   R   L>

1520          1530          1540          1550          1560          1570
         •             •             •             •             •             •
TAT TTA AAA GGT CAC ACT GGG ACA GCA GGA AAA CAG AGC AGC CTG ATC TTA CAC GGT GCT
 Y   L   K   G   H   T   G   T   A   G   K   Q   S   S   L   I   L   H   G   A>
```

Fig. 5D

```
        1580         1590         1600         1610         1620         1630
GAT TTC AGC ACT AAA GAT GCT GAT AAT GAC AAC TGT ATG TGC AAA TGT GCC CTC ATG TTA
 D   F   S   T   K   D   A   D   N   D   N   C   M   C   K   C   A   L   M   L>

1640         1650         1660         1670         1680         1690
ACA GGA GGA TGG TGG TTT GAT GCT TGT GGC CCC TCC AAT CTA AAT GGA ATG TTC TAT ACT
 T   G   G   W   W   F   D   A   C   G   P   S   N   L   N   G   M   F   Y   T>

1700         1710         1720         1730         1740         1750
CCG GGA CAA AAC CAT GGA AAA CTC AAT GGG ATA AAG TGG CAC TAC TTC AAA GGG CCC AGT
 A   G   Q   N   H   G   K   L   N   G   I   K   W   H   Y   F   K   G   P   S>

1760         1770         1780         1790         1800         1810
TAC TCC TTA CGT TCC ACA ACT ATG ATG ATT CGA CCT TTA GAT TTT TGA AAGCGCAATGTCAGAA
 Y   S   L   R   S   T   T   M   M   I   R   P   L   D   F   *>

1820        1830        1840        1850        1860        1870        1880        1890
GCGATTATGAAAGCAACAAAGAAATCCGCAGAAGCTGCCAGGTGAGAAACTGTTTGAAAACTTCAGAAGCAAACAATATT 1900        1910        1920        1930        1940        1950        1960        1970
CTCTCCCTTCCAGCAATAACTGGTAGTTATGTGAAGTCACCAAGCTTCTTGACCGTGAATCTGGAGCCGTTTGAGTTCAC 1980        1990        2000        2010        2020        2030        2040        2050
AACAGTCTCTACTTTGGGTGACAGTGCTCACGTGGCTCGACTATACAAAACTCCACTGACTGTCGGGCTTTAAAAAGGGA 2060        2070        2080        2090        2100        2110        2120        2130
AGAAACTGCTCAGCTTCCTGTGCTTCAAAACTACTACTGGACCTTATTTTCGAACTATGGTAGCCAGATGATAAATATGGT

2140
TAATTTC
```

Fig. 6A

```
         10        20        30        40        50        60        70        80
         •         •         •         •         •         •         •         •
GAATTCCTGGGTTGGTGTTTATCTCCTCCCAGCCTTGAGGGAGGGAACAACACTGTAGGATCTGGGGAGAGAGGAACAAA 90       100       110       120       130       140       150       160
         •         •         •         •         •         •         •         •
GGACCGTGAAAGCTGCTCTGTAAAAGCTGACACAGCCCTCCCAAGTGAGCAGGACTGTTCTTCCCACTGCAATCTGACAG 170       180       190       200       210       220       230       240
         •         •         •         •         •         •         •         •
TTTACTGCATGCCTGGAGAGAACACAGCAGTAAAAACCAGGTTTGCTACTGGAAAAAGAGGAAAGAGAAGACTTTCATTG 250       260       270       280       290       300       310       320
         •         •         •         •         •         •         •         •
ACGGACCCAGCCATGGCAGCGTAGCAGCCCTGCGTTTCAGACGGCAGCAGCTGGGACTCTGGACGTGTGTTTGCCCTCA 330       340       350       360       370       380
         •         •         •         •         •         •
AGTTTGCTAAGCTGCTGGTTTATTACTGAAGAAAGA ATG TGG CAG ATT GTT TTC TTT ACT CTG AGC TGT
                                      M   W   Q   I   V   F   F   T   L   S   C 390       400       410       420       430       440
    •         •         •         •         •         •
GAT CTT GTC TTG GCC GCA GCC TAT AAC AAC TTT CGG AAG AGC ATG GAC AGC ATA GGA AAG
 D   L   V   L   A   A   A   Y   N   N   F   R   K   S   M   D   S   I   G   K 450       460       470       480       490       500
 •         •         •         •         •         •
AAG CAA TAT CAG GTC CAG CAT GGG TCC TGC AGC TAC ACT TTC CTC CTG CCA GAG ATG GAC
 K   Q   Y   Q   V   Q   H   G   S   C   S   Y   T   F   L   L   P   E   M   D 510       520       530       540       550       560
 •         •         •         •         •         •
AAC TGC CGC TCT TCC TCC AGC CCC TAC GTG TCC AAT GCT GTG CAG AGG GAC GCG CCG CTC
 N   C   R   S   S   S   S   P   Y   V   S   N   A   V   Q   R   D   A   P   L 570       580       590       600       610       620
 •         •         •         •         •         •
GAA TAC GAT GAC TCG GTG CAG AGG CTG CAA GTG CTG GAG AAC ATC ATG GAA AAC AAC ACT
 E   Y   D   D   S   V   Q   R   L   Q   V   L   E   N   I   M   E   N   N   T
```

Fig. 6B

```
          630           640           650           660           670           680
           *             •             ▼             •             *             *
          CAG  TGG  CTA  ATG  AAG  CTT  GAG  AAT  TAT  ATC  CAG  GAC  AAC  ATG  AAG  AAA  GAA  ATG  GTA  GAG
           Q    W    L    M    K    L    E    N    Y    I    Q    D    N    M    K    K    E    M    V    E>

690           700           710           720          .730           740
           '             •             *             +             •             *
          ATA  CAG  CAG  AAT  GCA  GTA  CAG  AAC  CAG  ACG  GCT  GTG  ATG  ATA  GAA  ATA  GGG  ACA  AAC  CTG
           I    Q    Q    N    A    V    Q    N    Q    T    A    V    M    I    E    I    G    T    N    L>

750           760           770           780           790           800
           *             •             •             •             *             *
          TTG  AAC  CAA  ACA  GCT  GAG  CAA  ACG  CGG  AAG  TTA  ACT  GAT  GTG  GAA  GCC  CAA  GTA  TTA  AAT
           L    N    Q    T    A    E    Q    T    R    K    L   .T    D    V    E    A    Q    V    L    N>

810           820           830           840           850           860
           ▼             •             ▼             •             •             •
          CAG  ACC  ACG  AGA  CTT  GAA  CTT  CAG  CTC  TTG  GAA  CAC  TCC  CTC  TCG  ACA  AAC  AAA  TTG  GAA
           Q    T    T    R    L    E    L    Q    L    L    E    H    S    L    S    T    N    K    L    E>

870           880           890'          900           910           920
           *             •             •             •             •             •
          AAA  CAG  ATT  TTG  GAC  CAG  ACC  AGT  GAA  ATA  AAC  AAA  TTG  CAA  GAT  AAG  AAC  AGT  TTC  CTA
           K    Q    I    L    D    Q    T    S    E    I    N    K    L    Q    D    K    N    S    F    L>

930           940           950           960     '     970     '     980
           *             •             *             •             ▼             *
          GAA  AAG  AAG  GTG  CTA  GCT  ATG  GAA  GAC  AAG  CAC  ATC  ATC  CAA  CTA  CAG  TCA  ATA  AAA  GAA
           E    K    K    V    L    A    M    E    D    K    H    I    I    Q    L    Q    S    I    K    E>

990           1000          1010          1020          1030          1040
           •             •             •             •             •             •
          GAG  AAA  GAT  CAG  CTA  CAG  GTG  TTA  GTA  TCC  AAG  CAA  AAT  TCC  ATC  ATT  GAA  GAA  CTA  GAA
           E    K    D    Q    L    Q    V    L    V    S    K    Q    N    S    I    I    E    E    L    E>

050           1060          1070          1080          1090          1100
           •             •             •             •             •            .•
          AAA  AAA  ATA  GTG  ACT  GCC  ACG  GTG  AAT  AAT  TCA  GTT  CTT  CAA  AAG  CAG  CAA  CAT  GAT  CTC
           K    K    I    V    T    A    T    V    N    N    S    V    L    Q    K    Q    Q    H    D    L>
```

Fig. 6C

```
   1110        1120        1130        1140        1150        1160
ATG GAG ACA GTT AAT AAC TTA CTG ACT ATG ATG TCC ACA TCA AAC TCA GCT AAG GAC CCC
 M   E   T   V   N   N   L   L   T   M   M   S   T   S   N   S   A   K   D   P>

1170        1180        1190        1200        1210        1220
ACT GTT GCT AAA GAA GAA CAA ATC AGC TTC AGA GAC TGT GCT GAA GTA TTC AAA TCA GGA
 T   V   A   K   E   E   Q   I   S   F   R   D   C   A   E   V   F   K   S   G>

1230        1240        1250        1260        1270        1280
CAC ACC ACA AAT GGC ATC TAC ACG TTA ACA TTC CCT AAT TCT ACA GAA GAG ATC AAG GCC
 H   T   T   N   G   I   Y   T   L   T   F   P   N   S   T   E   E   I   K   A>

1290        1300        1310        1320        1330        1340
TAC TGT GAC ATG GAA GCT GGA GGA GGG GGG TGG ACA ATT ATT CAG CGA CGT GAG GAT GGC
 Y   C   D   M   E   A   G   G   G   G   W   T   I   I   Q   R   R   E   D   G>

1350        1360        1370        1380        1390        1400
AGC GTT GAT TTT CAG AGG ACT TGG AAA GAA TAT AAA GTG GGA TTT GGT AAC CCT TCA GGA
 S   V   D   F   Q   R   T   W   K   E   Y   K   V   G   F   G   N   P   S   G>

1410        1420        1430        1440        1450        1460
GAA TAT TGG CTG GGA AAT GAG TTT GTT TCG CAA CTG ACT AAT CAG CAA CGC TAT GTG CTT
 E   Y   W   L   G   N   E   F   V   S   Q   L   T   N   Q   Q   R   Y   V   L>

1470        1480        1490        1500        1510        1520
AAA ATA CAC CTT AAA GAC TGG GAA GGG AAT GAG GCT TAC TCA TTG TAT GAA CAT TTC TAT
 K   I   H   L   K   D   W   E   G   N   E   A   Y   S   L   Y   E   H   F   Y>

1530        1540        1550        1560        1570        1580
CTC TCA AGT GAA GAA CTC AAT TAT AGG ATT CAC CTT AAA GGA CTT ACA GGG ACA GCC GGC
 L   S   S   E   E   L   N   Y   R   I   H   L   K   G   L   T   G   T   A   G>
```

Fig. 6D

```
     1590          1600          1610          1620          1630          1640
      •             •             •             •             •             •
AAA ATA AGC AGC ATC AGC CAA CCA GGA AAT GAT TTT AGC ACA AAG GAT GGA GAC AAC GAC
 K   I   S   S   I   S   Q   P   G   N   D   F   S   T   K   D   G   D   N   D>

1650          1660          1670          1680          1690          1700
      •             •             •             •             •             •
AAA TGT ATT TGC AAA TGT TCA CAA ATG CTA ACA GGA GGC TGG TGG TTT GAT GCA TGT GGT
 K   C   I   C   K   C   S   Q   M   L   T   G   G   W   W   F   D   A   C   G>

1710          1720          1730          1740         ·1750          1760
      •             •             •             •             •             •
CCT TCC AAC TTG AAC GGA ATG TAC TAT CCA CAG AGG CAG AAC ACA AAT AAG TTC AAC GGC
 P   S   N   L   N   G   M   Y   Y   P   Q   R   Q   N   T   N   K   F   N   G>

1770          1780          1790          1800          1810          1820
      •             •             •             •             •             •
ATT AAA TGG TAC TAC TGG AAA GGC TCA GGC TAT TCG CTC AAG GCC ACA ACC ATG ATG ATC
 I   K   W   Y   Y   W   K   G   S   G   Y   S   L   K   A   T   T   M   M   I>

1830          1840          1850          1860          1870          1880          1890          1900
  •             •             •             •             •             •             •             •
CGA CCA GCA GAT TTC TAAACATCCCAGTCCACCTGAGGAACTGTCTCGAACTATTTTCAAAGACTTAAGCCCAGT
 R   P   A   D   F>

1910          1920          1930          1940          1950          1960          1970          1980
    •             •             •             •             •             •             •             •
GCACTGAAAGTCACGGCTGCGCACTGTGTCCTCTTCCACCACAGAGGGCGTGTGCTCGGTGCTGACGGGACCCACATGCT 1990          2000          2010          2020          2030          2040          2050          2060
    •             •             •             •             •             •             •             •
CCAGATTAGAGCCTGTAAACTTTATCACTTAAACTTGCATCACTTAACGGACCAAAGCAAGACCCTAAACATCCATAATT 2070          2080          2090          2100          2110          2120          2130          2140
    •             •             •             •             •             •             •             •
GTGATTAGACAGAACACCTATGCAAAGATGAACCCGAGGCTGAGAATCAGACTGACAGTTTACAGACGCTTCTGTCACAA 2150          2160          2170          2180          2190          2200          2210          2220
    •             •             •             •             •             •             •             •
CCAAGAATGTTATGTGCAAGTTTATCAGTAAATAACTGGAAAACAGAACACTTATGTTATACAATACAGATCATCTTGGA 2230          2240          2250          2260          2270          2280
    •             •             •             •             •             •
ACTGCATTCTTCTGAGCACTGTTTATACACTGTGTAAATACCCATATGTCCTGAATTC
```

TIE-2 LIGANDS, METHODS OF MAKING AND USES THEREOF

CROSS-REFERENCE TO RELATED APPLICATIONS

This application is a divisional of U.S. Ser. No. 08/817,318 filed Sep. 16, 1999, which claims priority of U.S. Applications U.S. Ser. No. 08/418,595, filed Apr. 6, 1995, now U.S. Pat. No. 5,814,464, which is a continuation-in-part of U.S. Ser. No. 08/373,579, filed Jan. 17, 1995, now U.S. Pat. No. 5,650,490, which is a continuation-in-part of U.S. Ser. No. 08/353,503, filed Dec. 9, 1994, now abandoned, which is a continuation-in-part of U.S. Ser. No. 08/348,492, filed Dec. 2, 1994, now U.S. Pat. No. 5,879,672, which is a continuation-in-part of U.S. Ser. No. 08/330,261 filed Oct. 27, 1994, now U.S. Pat. No. 5,521,073, which is a continuation-in-part of U.S. Ser. No. 08/319,932, filed Oct. 7, 1994, now U.S. Pat. No. 5,643,755, the contents of each of which are hereby incorporated by reference.

INTRODUCTION

The present invention relates generally to the field of genetic engineering and more particularly to genes for receptor tyrosine kinases and their cognate ligands, their insertion into recombinant DNA vectors, and the production of the encoded proteins in recipient strains of micro-organisms and recipient eukaryotic cells. More specifically, the present invention is directed to novel ligands, known as the TIE-2 ligands, that bind the TIE-2 receptor, as well as to methods of making and using the TIE-2 ligands. The invention further provides nucleic acid sequences encoding TIE-2 ligands, and methods for the generation of nucleic acids encoding TIE-2 ligands and their gene products. The TIE-2 ligands, as well as nucleic acids encoding them, may be useful in the diagnosis and treatment of certain diseases involving endothelial cells and associated TIE receptors, such as neoplastic diseases involving tumor angiogenesis, wound healing, thromboembolic diseases, atherosclerosis and inflammatory diseases. More generally, biologically active TIE-2 ligands may be used to promote the growth, survival and/or differentiation of cells expressing the TIE-2 receptor. Biologically active TIE-2 ligand may be used for the in vitro maintenance of TIE-2 receptor expressing cells in culture. Cells and tissues expressing TIE-2 receptor include, for example, cardiac and vascular endothelial cells, lens epithelium and heart epicardium. Alternatively, such ligand may be used to support cells which are engineered to express TIE-2 receptor. Further, TIE-2 ligands and their cognate receptor may be used in assay systems to identify agonists or antagonists of the TIE-2 receptor.

BACKGROUND OF THE INVENTION

The cellular behavior responsible for the development, maintenance, and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long-term readjustment of cellular gene expression. Several receptors associated with various cell surfaces may bind specific growth factors.

The phosphorylation of tyrosines on proteins by tyrosine kinases is one of the key modes by which signals are transduced across the plasma membrane. Several currently known protein tyrosine kinase genes encode transmembrane receptors for polypeptide growth factors and hormones such as epidermal growth factor (EGF), insulin, insulin-like growth factor-I (IGF-I), platelet derived growth factors (PDGF-A and -B), and fibroblast growth factors (FGFs). (Heldin et al., Cell Regulation, 1: 555–566 (1990); Ullrich, et al., Cell, 61: 243–54 (1990)). In each instance, these growth factors exert their action by binding to the extracellular portion of their cognate receptors, which leads to activation of the intrinsic tyrosine kinase present on the cytoplasmic portion of the receptor. Growth factor receptors of endothelial cells are of particular interest due to the possible involvement of growth factors in several important physiological and pathological processes, such as vasculogenesis, angiogenesis, atherosclerosis, and inflammatory diseases. (Folkman, et al. Science, 235: 442–447 (1987)). Also, the receptors of several hematopoietic growth factors are tyrosine kinases; these include c-fms, which is the colony stimulating factor 1 receptor, Sherr, et al., Cell, 41: 665–676 (1985), and c-kit, a primitive hematopoietic growth factor receptor reported in Huang, et al., Cell, 63: 225–33 (1990).

The receptor tyrosine kinases have been divided into evolutionary subfamilies based on the characteristic structure of their ectodomains. (Ullrich, et al. Cell, 61: 243–54 (1990)). Such subfamilies include, EGF receptor-like kinase (subclass I) and insulin receptor-like kinase (subclass II), each of which contains repeated homologous cysteine-rich sequences in their extracellular domains. A single cysteine-rich region is also found in the extracellular domains of the eph-like kinases. Hirai, et al., Science, 238: 1717–1720 (1987); Lindberg, et al. Mol. Cell. Biol., 10: 6316–24 (1990); Lhotak, et al., Mol. Cell. Biol. 11: 2496–2502 (1991). PDGF receptors as well as c-fms and c-kit receptor tyrosine kinases may be grouped into subclass III; while the FGF receptors form subclass IV. Typical for the members of both of these subclasses are extracellular folding units stabilized by intrachain disulfide bonds. These so-called immunoglobulin (Ig)-like folds are found in the proteins of the immunoglobulin superfamily which contains a wide variety of other cell surface receptors having either cell-bound or soluble ligands. Williams, et al., Ann. Rev. Immunol., 6: 381–405 (1988).

Receptor tyrosine kinases differ in their specificity and affinity. In general, receptor tyrosine kinases are glycoproteins, which consist of (1) an extracellular domain capable of binding the specific growth factor(s); (2) a transmembrane domain which usually is an alpha-helical portion of the protein; (3) a juxtamembrane domain where the receptor may be regulated by, e.g., protein phosphorylation; (4) a tyrosine kinase domain which is the enzymatic component of the receptor; and (5) a carboxyterminal tail which in many receptors is involved in recognition and binding of the substrates for the tyrosine kinase.

Processes such as alternative exon splicing and alternative choice of gene promoter or polyadenylation sites have been reported to be capable of producing several distinct polypeptides from the same gene. These polypeptides may or may not contain the various domains listed above. As a consequence, some extracellular domains may be expressed as separate, secreted proteins and some forms of the receptors may lack the tyrosine kinase domain and contain only the extracellular domain inserted in the plasma membrane via the transmembrane domain plus a short carboxyl terminal tail.

A gene encoding an endothelial cell transmembrane tyrosine kinase, originally identified by RT-PCR as an unknown tyrosine kinase-homologous cDNA fragment from human leukemia cells, was described by Partanen, et al., Proc. Natl. Acad. Sci. USA, 87: 8913–8917 (1990). This gene and its encoded protein are called "tie" which is an abbreviation for "tyrosine kinase with Ig and EGF homology domains." Partanen, et al. Mol. Cell. Biol. 12: 1698–1707 (1992).

It has been reported that tie mRNA is present in all human fetal and mouse embryonic tissues. Upon inspection, tie message has been localized to the cardiac and vascular endothelial cells. tie mRNA has been localized to the endothelia of blood vessels and endocardium of 9.5 to 18.5 day old mouse embryos. Enhanced tie expression was shown during neovascularization associated with developing ovarian follicles and granulation tissue in skin wounds. Korhonen, et al. Blood 80: 2548–2555 (1992). Thus tie has been suggested to play a role in angiogenesis, which is important for developing treatments for solid tumors and several other angiogenesis-dependent diseases such as diabetic retinopathy, psoriasis, atherosclerosis and arthritis.

Two structurally related rat TIE receptor proteins have been reported to be encoded by distinct genes with related profiles of expression. One gene, termed tie-1, is the rat homolog of human tie. Maisonpierre, et al., Oncogene 8: 1631–1637 (1993). The other gene, tie-2, may be the rat homolog of the murine tek gene, which, like tie, has been reported to be expressed in the mouse exclusively in endothelial cells and their presumptive progenitors. Dumont, et al. Oncogene 8: 1293–1301 (1993).

Both genes were found to be widely expressed in endothelial cells of embryonic and postnatal tissues. Significant levels of tie-2 transcripts were also present in other embryonic cell populations, including lens epithelium, heart epicardium and regions of mesenchyme. Maisonpierre, et al., Oncogene 8: 1631–1637 (1993).

The predominant expression of the TIE receptor in vascular endothelia suggests that TIE plays a role in the development and maintenance of the vascular system. This could include roles in endothelial cell determination, proliferation, differentiation and cell migration and patterning into vascular elements. It has been reported that analyses of mouse embryos deficient in TIE-2 showed that it is important in angiogenesis, particular for vascular network formation in endothelial cells. Sato, T. N., et al., Nature 376:70–74 (1994). In the mature vascular system, TIE could function in endothelial cell survival, maintenance and response to pathogenic influences.

SUMMARY OF THE INVENTION

The present invention provides for a composition comprising a TIE-2 ligand substantially free of other proteins. The invention also provides for an isolated nucleic acid molecule encoding a TIE-2 ligand. The isolated nucleic acid may be DNA, cDNA or RNA. The invention also provides for a vector comprising an isolated nucleic acid molecule encoding a TIE-2 ligand. The invention further provides for a host-vector system for the production in a suitable host cell of a polypeptide having the biological activity of a TIE-2 ligand. The suitable host cell may be bacterial, yeast, insect or mammalian. The invention also provides for a method of producing a polypeptide having the biological activity of a TIE-2 ligand which comprises growing cells of the host-vector system under conditions permitting production of the polypeptide and recovering the polypeptide so produced.

The invention herein described of an isolated nucleic acid molecule encoding a TIE-2 ligand further provides for the development of the ligand, a fragment or derivative thereof, or another molecule which is a receptor agonist or antagonist, as a therapeutic for the treatment of patients suffering from disorders involving cells, tissues or organs which express the TIE receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The present invention also provides for an antibody which specifically binds a TIE-2 ligand. The antibody may be monoclonal or polyclonal. Thus the invention further provides for therapeutic compositions comprising an antibody which specifically binds a TIE-2 ligand in a pharmaceutically acceptable vehicle. The invention also provides for a method of blocking blood vessel growth in a mammal by administering an effective amount of a therapeutic composition comprising an antibody which specifically binds a TIE-2 ligand in a pharmaceutically acceptable vehicle.

The invention further provides for therapeutic compositions comprising a TIE-2 ligand in a pharmaceutically acceptable vehicle. The invention also provides for a method of promoting neovascularization in a patient by administering an effective amount of a therapeutic composition comprising a TIE-2 ligand in a pharmaceutically acceptable vehicle. In one embodiment, the method may be used to promote wound healing. In another embodiment, the method may be used to treat ischemia.

Alternatively, the invention provides that a TIE-2 ligand may be conjugated to a cytotoxic agent and a therapeutic composition prepared therefrom. The invention further provides for a receptor body which specifically binds a TIE-2 ligand. The invention further provides for therapeutic compositions comprising a receptor body which specifically binds a TIE-2 ligand in a pharmaceutically acceptable vehicle. The invention also provides for a method of blocking blood vessel growth in a mammal by administering an effective amount of a therapeutic composition comprising a receptor body which specifically binds a TIE-2 ligand in a pharmaceutically acceptable vehicle.

The invention also provides for a TIE-2 receptor antagonist as well as a method of inhibiting TIE-2 ligand biological activity in a mammal comprising administering to the mammal an effective amount of a TIE-2 antagonist. According to the invention, the antagonist may be an antibody or other molecule capable of specifically binding either TIE-2 ligand or TIE-2 receptor. For example, the antagonist may be a TIE-2 receptorbody.

BRIEF DESCRIPTION OF THE FIGURES

FIG. 1A: embryos treated with EHK-1 RB (rEHK-1 ecto/h IgG1 Fc) were viable and possessed normally developed blood vessels in their surrounding CAM. FIG. 1B: all embryos treated with TIE-2 RB (r TIE-2 ecto/h IgG1 Fc) were dead, diminished in size and were almost completely devoid of surrounding blood vessels.

FIGS. 4A–4D (SEQ ID NOS: 1 and 2)-Nucleic acid (SEQ ID NO: 1) and deduced amino acid (single letter code) sequences (SEQ ID NO: 2) of human TIE-2 ligand from clone λgt10 encoding htie-2 ligand 1.

FIGS. 5A–5D (SEQ ID NOS: 3 and 4)-Nucleic acid (SEQ ID NO: 3) and deduced amino acid (single letter code) sequences (SEQ ID NO: 4) of human TIE-2 ligand from T98G clone.

FIGS. 6A–6D (SEQ ID NOS: 5 and 6)-Nucleic acid (SEQ ID NO: 5) and deduced amino acid (single letter code) sequences (SEQ ID NO: 6) of human TIE-2 ligand from clone pBluescript KS encoding human TIE 2 ligand 2.

DETAILED DESCRIPTION OF THE INVENTION

Figure 1A:
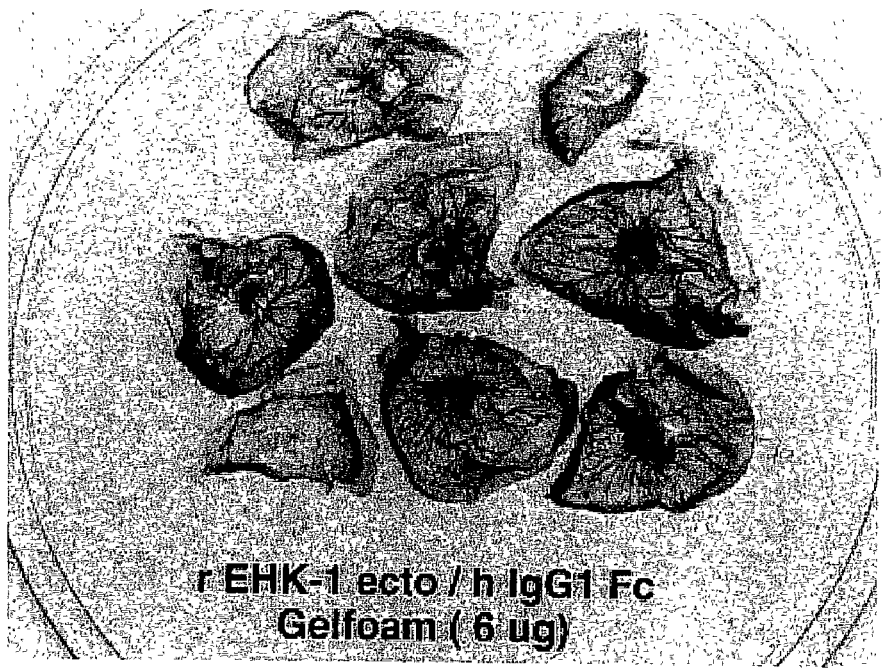
FIGS. 1A and 1B—TIE-2 receptorbody (TIE-2 RB) inhibits the development of blood vessels in the embryonic chicken chorioallantoic membrane (CAM). A single piece of resorbable gelatin foam (Gelfoam) soaked with 6 μg of RB was inserted immediately under the CAM of 1-day chick embryos. After 3 further days of incubation, 4 day old embryos and surrounding CAM were removed and examined.

As described in greater detail below, applicants have isolated, by expression cloning, a novel ligand that binds the TIE-2 receptor. The present invention comprises a TIE-2 ligand as well as its amino acid sequence and also functionally equivalent molecules in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

The present invention also encompasses the nucleotide sequence that encodes the protein described herein as TIE-2 ligand 1, as well as cells which are genetically engineered to produce the protein, by e.g. transfection, transduction, infection, electroporation, or microinjection of nucleic acid encoding the TIE-2 ligand 1 described herein in a suitable expression vector.

The present invention further encompasses the nucleotide sequence that encodes the protein described herein as TIE-2 ligand 2, as well as cells which are genetically engineered to produce the protein, by e.g. transfection, transduction, infection, electroporation, or microinjection of nucleic acid encoding the TIE-2 ligand 2 described herein in a suitable expression vector.

One skilled in the art will also recognize that the present invention encompasses DNA and RNA sequences that hybridize to a deduced TIE-2 ligand encoding sequence, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, a nucleic acid molecule contemplated by the invention includes one having a sequence deduced from an amino acid sequence of a TIE-2 ligand prepared as described herein, as well as a molecule having a sequence of nucleic acids that hybridizes to such a nucleic acid sequence, and also a nucleic acid sequence which is degenerate of the above sequences as a result of the genetic code, but which encodes a ligand that binds the TIE-2 receptor.

Any of the methods known to one skilled in the art for the insertion of DNA fragments into a vector may be used to construct expression vectors encoding TIE-2 ligand using appropriate transcriptional/translational control signals and the protein coding sequences. These methods may include in vitro recombinant DNA and synthetic techniques and in vivo recombinations (genetic recombination). Expression of a nucleic acid sequence encoding a TIE-2 ligand or peptide fragments thereof may be regulated by a second nucleic acid sequence so that the protein or peptide is expressed in a host transformed with the recombinant DNA molecule. For example, expression of a TIE-2 ligand described herein may be controlled by any promoter/enhancer element known in the art. Promoters which may be used to control expression of the ligand include, but are not limited to the long terminal repeat as described in Squinto et al., (Cell 65:1–20 (1991)); the SV40 early promoter region (Bernoist and Chambon, Nature 290:304–310), the CMV promoter, the M-MULV 5' terminal repeat, the promoter contained in the 3' long terminal repeat of Rous sarcoma virus (Yamamoto, et al., Cell 22:787–797 (1980)), the herpes thymidine kinase promoter (Wagner et al., Proc. Natl. Acad. Sci. U.S.A. 78:144–1445 (1981)), the adenovirus promoter, the regulatory sequences of the metallothioein gene (Brinster et al., Nature 296:39–42 (1982)); prokaryotic expression vectors such as the β-lactamase promoter (Villa-Kamaroff, et al., Proc. Natl. Acad. Sci. U.S.A. 75:3727–3731 (1978)), or the tac promoter (DeBoer, et al., Proc. Natl. Acad. Sci. U.S.A. 80:21–25 (1983)), see also "Useful proteins from recombinant bacteria" in Scientific American, 242:74–94 (1980); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., Cell 38:639–646 (1984); Ornitz et al., Cold Spring Harbor Symp. Quant. Biol. 50:399–409 (1986); MacDonald, Hepatology 7:425–515 (1987); insulin gene control region which is active in pancreatic beta cells (Hanahan, Nature 315: 115–122 (1985)), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378). The invention further encompasses the production of antisense compounds which are capable of specifically hybridizing with a sequence of RNA encoding a TIE-2 ligand to modulate its expression. (Ecker, U.S. Pat. No. 5,166,195, issued Nov. 24, 1992).

Thus, according to the invention, expression vectors capable of being replicated in a bacterial or eukaryotic host comprising a nucleic acid encoding a TIE-2 ligand as described herein, are used to transfect a host and thereby direct expression of such nucleic.acid to produce the TIE-2 ligand, which may then be recovered in a biologically active form. As used herein, a biologically active form includes a form capable of binding to the TIE-2 receptor and causing a biological response such as a differentiated function or influencing the phenotype of the cell expressing the receptor. Such biologically active forms would, for example, induce phosphorylation of the tyrosine kinase domain of the TIE-2 receptor.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted TIE-2 ligand encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if a nucleic acid encoding a TIE-2 ligand is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of a TIE-2 ligand gene product, for example, by binding of the ligand to the TIE-2 receptor or portion thereof which may be tagged with, for example, a detectable antibody or portion thereof or by binding to antibodies produced against the TIE-2 ligand protein or a portion thereof. Cells of the present invention may transiently or, preferably, constitutively and permanently express TIE-2 ligands as described herein. In the fourth approach, DNA nucleotide primers can be prepared corresponding to a tie-2 specific DNA sequence. These primers could then be used to PCR a tie-2 gene fragment. (PCR Protocols: A Guide To Methods and Applications, Edited by Michael A. Innis et al., Academic Press (1990)).

The recombinant ligand may be purified by any technique which allows for the subsequent formation of a stable, biologically active protein. For example, and not by way of limitation, the ligand may be recovered from cells either as soluble proteins or as inclusion bodies, from which they may be extracted quantitatively by 8M guanidinium hydrochloride and dialysis. In order to further purify the ligand, conventional ion exchange chromatography, hydrophobic interaction chromatography, reverse phase chromatography or gel filtration may be used.

In additional embodiments of the invention, a recombinant TIE-2 ligand encoding gene may be used to inactivate or "knock out" the endogenous gene by homologous recombination, and thereby create a TIE-2 ligand deficient cell, tissue, or animal. For example, and not by way of limitation, the recombinant TIE-2 ligand encoding gene may be engineered to contain an insertional mutation, for example the neo gene, which would inactivate the native TIE-2 ligand encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE-2 ligand encoding gene may then be identified, e.g. by Southern blotting, PCR detection, Northern blotting or assay of expression. Cells lacking an intact TIE-2 ligand encoding gene may then be fused to early embryo cells to generate transgenic animals deficient in such ligand. Such an animal may be used to define specific in vivo processes, normally dependent upon the ligand.

The present invention also provides for antibodies to the TIE-2 ligands described herein which are useful for detection of the ligands in, for example, diagnostic applications For preparation of monoclonal antibodies directed toward TIE-2 ligand, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies. or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the TIE-2 ligands described herein. For the production of antibody, various host animals can be immunized by injection with a TIE-2 ligand, or a fragment or derivative thereof, including but not limited to rabbits, mice and rats. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected TIE-2 ligand epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The present invention further encompasses an immunoassay for measuring the amount of a TIE-2 ligand in a biological sample by
a) contacting the biological sample with at least one antibody which specifically binds the TIE-2 ligand so that the antibody forms a complex with any TIE-2 ligand present in the sample; and
b) measuring the amount of the complex and thereby measuring the amount of the TIE-2 ligand in the biological sample.

The invention further encompasses an assay for measuring the amount of TIE-2 receptor in a biological sample by
a) contacting the biological sample with at least one ligand of the invention so that the ligand forms a complex with the TIE-2 receptor; and
b) measuring the amount of the complex and thereby measuring the amount of the TIE-2 receptor in the biological sample.

The present invention also provides for the utilization of a TIE-2 ligand to support the survival and/or growth and/or differentiation of TIE-2 receptor expressing cells. Thus, the ligand may be used as a supplement to support, for example, endothelial cells in culture. Further, the discovery by applicants of a cognate ligand for the TIE-2 receptor enables the utilization of assay systems useful for the identification of agonists or antagonists of the TIE-2 receptor. Such assay systems would be useful in identifying molecules capable of promoting or inhibiting angiogenesis. For example, in one embodiment, antagonists of the TIE-2 receptor may be identified as test molecules that are capable of interfering with the interaction of the TIE-2 receptor with a biologically active TIE-2 ligand. Such antagonists are identified by their ability to 1) block the binding of a biologically active TIE-2 ligand to the receptor as measured, for example, using BIAcore biosensor technology (BIAcore; Pharmacia Biosensor, Piscataway, N.J.); or 2) block the ability of a biologically active TIE-2 ligand to cause a biological response. Such biological responses include, but are not limited to, phosphorylation of the TIE-2 receptor or downstream components of the TIE-2 signal transduction pathway, or survival, growth or differentiation of TIE-2 receptor bearing cells.

In one embodiment, cells engineered to express the TIE-2 receptor may be dependent for growth on the addition of TIE-2 ligand. Such cells provide useful assay systems for identifying additional agonists of the TIE-2 receptor, or antagonists capable of interfering with the activity of TIE-2 ligand on such cells. Alternatively, autocrine cells, engineered to be capable of co-expressing both TIE-2 ligand and receptor, may provide useful systems for assaying potential agonists or antagonists.

Therefore, the present invention provides for introduction of the TIE-2 receptor into cells that do not normally express this receptor, thus allowing these cells to exhibit profound and easily distinguishable responses to a ligand which binds this receptor. The type of response elicited depends on the cell utilized, and not the specific receptor introduced into the cell. Appropriate cell lines can be chosen to yield a response of the greatest utility for assaying, as well as discovering, molecules that can act on tyrosine kinase receptors. The molecules may be any type of molecule, including but not limited to peptide and non-peptide molecules, that will act in systems to be described in a receptor specific manner.

One of the more useful systems to be exploited involves the introduction of the TIE-2 receptor into a fibroblast cell line (e.g., NIH3T3 cells) thus such a receptor which does not normally mediate proliferative responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor. Such cells may be further engineered to express the TIE-2 ligand, thus creating an autocrine system useful for assaying for molecules that act as antagonists/agonists of this interaction. Thus, the present invention provides for host cells comprising nucleic acid encoding TIE-2 ligand and nucleic acid encoding TIE-2 receptor.

The TIE-2 receptor/TIE-2 ligand interaction also provides a useful system for identifying small molecule agonists or antagonists of the TIE-2 receptor. For example, fragments, mutants or derivatives of a TIE-2 ligand may be identified that bind the TIE-2 receptor but do not induce biological activity. Alternatively, the characterization of a TIE-2 ligand enables the determination of active portions of the molecule. Further, the identification of a ligand enables the determination of the X-ray crystal structure of the receptor/ligand complex, thus enabling identification of the binding site on the receptor. Knowledge of the binding site will provide useful insight into the rational design of novel agonists and antagonists.

The specific binding of a test molecule to the TIE-2 receptor may be measured in a number of ways. For example, the actual binding of test molecule to cells expressing tie-2 may be detected or measured, by detecting or measuring (i) test molecule bound to the surface of intact cells; (ii) test molecule cross-linked to TIE-2 protein in cell lysates; or (iii) test molecule bound to TIE-2 in vitro. The specific interaction between test molecule and TIE-2 may be evaluated by using reagents that demonstrate the unique properties of that interaction.

As a specific, nonlimiting example, the methods of the invention may be used as follows. Consider a case in which the TIE-2 ligand in a sample is to be measured. Varying dilutions of the sample (the test molecule), in parallel with a negative control (NC) containing no TIE-2 ligand activity, and a positive control (PC) containing a known amount of a TIE-2 ligand, may be exposed to cells that express tie-2 in the presence of a detectably labeled TIE-2 ligand (in this example, radioiodinated ligand). The amount of TIE-2 ligand in the test sample may be evaluated by determining the amount of $^{125}$I-labeled TIE-2 ligand that binds to the controls and in each of the dilutions, and then comparing the sample values to a standard curve. The more TIE-2 ligand in the sample, the less $^{125}$I-ligand that will bind to TIE-2.

The amount of $^{125}$I-ligand bound may be determined by measuring the amount of radioactivity per cell, or by cross-linking the TIE-2 ligand to cell surface proteins using DSS, as described in Meakin and Shooter, 1991, Neuron 6:153–163, and detecting the amount of labeled protein in cell extracts using, for example, SDS polyacrylamide gel electrophoresis, which may reveal a labeled protein having a size corresponding to TIE-2 ligand/TIE-2 receptor. The specific test molecule/TIE-2 interaction may further be tested by adding to the assays various dilutions of an unlabeled control ligand that does not bind the TIE-2 receptor and therefore should have no substantial affect on the competition between labeled TIE-2 ligand and test molecule for TIE-2 binding. Alternatively, a molecule known to be able to disrupt TIE-2 ligand/TIE-2 binding, such as, but not limited to, anti-TIE-2 antibody, or TIE-2 receptorbody as described herein, may be expected to interfere with the competition between $^{125}$I-TIE-2 ligand and test molecule for TIE-2 receptor binding.

Detectably labeled TIE-2 ligand includes, but is not limited to, TIE-2 ligand linked covalently or noncovalently to a radioactive substance, a fluorescent substance, a substance that has enzymatic activity, a substance that may serve as a substrate for an enzyme (enzymes and substrates associated with calorimetrically detectable reactions are preferred) or to a substance that can be recognized by an antibody molecule that is preferably a detectably labeled antibody molecule.

Alternatively, the specific binding of test molecule to TIE-2 may be measured by evaluating the secondary biological effects of TIE-2 ligand/TIE-2 receptor binding, including, but not limited to, cell growth and/or differentiation or immediate early gene expression or phosphorylation of TIE-2. For example, the ability of the test molecule to induce differentiation can be tested in cells that lack tie-2 and in comparable cells that express tie-2; differentiation in tie-2-expressing cells but not in comparable cells that lack tie-2 would be indicative, of a specific test molecule/TIE-2 interaction. A similar analysis could be performed by detecting immediate early gene (e.g. fos and jun) induction in tie-2-minus and tie-2-plus cells, or by detecting phosphorylation of TIE-2 using standard phosphorylation assays known in the art. Such analysis might be useful in identifying agonists or antagonists that do not competitively bind to TIE-2.

Similarly, the present invention provides for a method of identifying an molecule that has the biological activity of a TIE-2 ligand comprising (i) exposing a cell that expresses tie-2 to a test molecule and (ii) detecting the specific binding of the test molecule to TIE-2 receptor, in which specific binding to TIE-2 positively correlates with TIE-2 like activity. Specific binding may be detected by either assaying for direct binding or the secondary biological effects of binding, as discussed supra. Such a method may be particularly useful in identifying new members of the TIE ligand family or, in the pharmaceutical industry, in screening a large array of peptide and non-peptide molecules (e.g., peptidomimetics) for TIE associated biological activity. In a preferred, specific, nonlimiting embodiment of the invention, a large grid of culture wells may be prepared that contain, in alternate rows, PC12 (or fibroblasts, see infra) cells that are either tie-2-minus or engineered to be tie-2-plus. A variety of test molecules may then be added such that each column of the grid, or a portion thereof, contains a different test molecule. Each well could then be scored for the presence or absence of growth and/or differentiation. An extremely large number of test molecules could be screened for such activity in this manner.

In additional embodiments, the invention provides for methods of detecting or measuring TIE-like activity or identifying a molecule as having such activity comprising (i) exposing a test molecule to a TIE-2 receptor protein in vitro under conditions that permit binding to occur and (ii) detecting binding of the test molecule to the TIE-2 protein, in which binding of test molecule to TIE-2 correlates with TIE-like activity. According to such methods, the TIE-2 may or may not be substantially purified, may be affixed to a solid support (e.g. as an affinity column or as an ELISA assay), or may be incorporated into an artificial membrane. Binding of test molecule to TIE-2 may be evaluated by any method known in the art. In preferred embodiments, the binding of test molecule may be detected or measured by evaluating its ability to compete with detectably labeled known TIE-2 ligands for TIE-2 receptor binding.

The present invention also provides for a method of detecting the ability of a test molecule to function as an antagonist of TIE-like activity comprising detecting the ability of the molecule to inhibit an effect of TIE ligand binding to TIE-2 on a cell that expresses tie-2. Such an antagonist may or may not interfere with TIE-2 ligand/TIE-2 receptor binding. Effects of TIE-2 ligand binding to TIE-2 receptor are preferably biological or biochemical effects, including, but not limited to, cell survival or proliferation, cell transformation, immediate early gene induction, or TIE-2 phosphorylation.

The invention further provides for both a method of identifying antibodies or other molecules capable of neutralizing the ligand or blocking binding to the receptor, as well as the molecules identified by the method. By way of nonlimiting example, the method may be performed via an assay which is conceptually similar to an ELISA assay. For example, TIE receptorbody may be bound to a solid support, such as a plastic multiwell plate. As a control, a known amount of TIE ligand which has been Myc-tagged may then be introduced to the well and any tagged TIE ligand which binds the receptorbody may then be identified by means of a reporter antibody directed against the Myc-tag. This assay system may then be used to screen test samples for molecules which are capable of i) binding to the tagged ligand or ii) binding to the receptorbody and thereby blocking binding to the receptorbody by the tagged ligand. For example, a test sample containing a putative molecule of interest together with a known amount of tagged ligand may be introduced to the well and the amount of tagged ligand which binds to the receptorbody may be measured. By comparing the amount of bound tagged ligand in the test sample to the amount in the control, samples containing molecules which are capable of blocking ligand binding to the receptor may be identified. The molecules of interest thus identified may be isolated using methods well known to one of skill in the art.

Once a blocker of ligand binding is found, one of skill in the art would know to perform secondary assays to determine whether the blocker is binding to the receptor or to the ligand, as well as assays to determine if the blocker molecule can neutralize the biological activity of the ligand. For example, by using a binding assay which employs BIAcore biosensor technology (or the equivalent), in which either TIE receptorbody or TIE ligand is covalently attached to a solid support (e.g. carboxymethyl dextran on a gold surface), one of skill in the art would be able to determine if the blocker molecule is binding specifically to the ligand or to the receptorbody. To determine if the blocker molecule can neutralize the biological activity of the ligand, one of skill in the art could perform a phosphorylation assay (see Example 5) or alternatively, a functional bioassay, such as a survival assay, by using primary cultures of, for example, endothelial cells. Alternatively, a blocker molecule which binds to the receptorbody could be an agonist and one of skill in the art would know to how to determine this by performing an appropriate assay for identifying additional agonists of the TIE-2 receptor.

Because TIE-2 receptor has been identified in association with endothelial cells and, as demonstrated herein, blocking of the ligand appears to prevent vascularization, applicants have demonstrated that the TIE-2 ligand will be useful for the induction of vascularization in diseases or disorders where such vascularization is indicated. Such diseases or disorders would include wound healing, ischaemia and diabetes. On the other hand, antagonists of the TIE-2 receptor, such as receptorbodies as described herein in Examples 2 and 3, and TIE-2 ligand 2 as described in Example 9, would be useful to prevent or attenuate vascularization, thus preventing or attenuating, for example, tumor growth.

Because TIE-2 receptor bearing cells appear to be upregulated in vascularization, TIE-2 ligandbodies may also be useful in preventing or attenuating, for example, tumor growth. TIE-2 ligandbodies may be useful for the delivery of toxins to a receptor bearing cell. Alternatively, other molecules, such as growth factors, cytokines or nutrients, may be delivered to a TIE-2 receptor bearing cell via TIE-2 ligandbodies. TIE-2 ligandbodies could also be used as a diagnostic reagent for the TIE-2 receptor, to detect the receptor in vivo or in vitro. Where the TIE-2 receptor is associated with a disease state, TIE-2 ligandbodies may be useful as diagnostic reagents for detecting the disease by, for example, tissue staining or whole body imaging.

The present invention also provides for pharmaceutical compositions comprising the TIE-2 ligands or ligandbodies described herein, peptide fragments thereof, or derivatives in a pharmacologically acceptable vehicle. The TIE-2 ligand proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention further provides for an isolated and purified nucleic acid molecule comprising a nucleic acid sequence encoding a human TIE-2 ligand, wherein the nucleic acid sequence is selected from the group consisting of:

(a) the nucleic acid sequence comprising the coding region of the human TIE-2 ligand as set forth in FIGS. 4A–4D (SEQ ID NO: 1), FIGS. 5A–5D (SEQ ID NO: 3) or FIGS. 6A–6D (SEQ ID NO: 5);

(b) a nucleic acid sequence that hybridizes under moderately stringent conditions to the nucleic acid sequence of (a) and which encodes a TIE-2 ligand that binds TIE-2 receptor; and (c) a nucleic acid sequence that is degenerate as a result of the genetic code to a nucleic acid sequence of (a) or (b), and which encodes a TIE-2 ligand that binds TIE-2 receptor.

In another embodiment the invention provides for an isolated nucleic acid molecule encoding a TIE-2 ligand wherein the nucleic acid sequence is:

(a) the nucleic acid sequence comprising the coding region of the human TIE-2 ligand as set forth in FIGS. 4A–4D (SEQ ID NO: 1), FIGS. 5A–5D (SEQ ID NO: 3) or FIGS. 6A–6D (SEQ ID NO: 5);

(b) a nucleic acid sequence that hybridizes under moderately stringent conditions to the nucleic acid sequence of (a) and which encodes a TIE-2 ligand that binds TIE-2 receptor; or (c) a nucleic acid sequence which, but for the degeneracy of the genetic code would hybridize to a nucleic acid sequence of (a) or (b), and which encodes a TIE-2 ligand that binds TIE-2 receptor.

The present invention further provides for an isolated and purified human TIE-2 ligand encoded by an isolated nucleic acid molecule of the invention. The invention also provides a vector which comprises an isolated nucleic acid molecule comprising a nucleic acid sequence encoding a human TIE-2 ligand. In one embodiment, the vector is designated as pBluescript KS encoding human TIE 2 ligand 2.

The invention further provides for an expression vector comprising a DNA molecule encoding a human TIE-2 ligand, wherein the DNA molecule is operatively linked to an expression control sequence. The invention also provides a host-vector system for the production of a polypeptide having the biological activity of a human TIE-2 ligand which comprises the expression vector of the invention in a suitable host cell. In one embodiment, the suitable host cell may be a bacterial cell, yeast cell, insect cell, or mammalian cell. The invention further provides for a method of producing a polypeptide having the activity of a biologically active TIE-2 ligand which comprises growing cells of the host-vector system of the invention, under conditions permitting production of the polypeptide and recovering the polypeptide so produced.

The invention herein described of an isolated nucleic acid molecule encoding a TIE-2 ligand further provides for the development of the ligand, a fragment or derivative thereof, or another molecule which is a receptor agonist or antagonist, as a therapeutic for the treatment of patients suffering from disorders involving cells, tissues or organs which express the TIE receptor. By way of nonlimiting example, the present invention provides for a ligandbody which specifically binds the TIE-2 receptor or the TIE-2. In an alternative embodiment, the present invention provides for a ligandbody which comprises a TIE-2 ligand fused to an immunoglobulin constant region. In one embodiment, the ligandbody comprises TIE-2 ligand 1 or TIE-2 ligand 2 and the Fc portion of human IgG1. The ligandbody may be used in a method of treatment of the human or animal body, or in a method of diagnosis.

The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The invention further provides for a therapeutic composition comprising a human TIE-2 ligand or ligandbody and a cytotoxic agent conjugated thereto. In one embodiment, the cytotoxic agent may be a radioisotope or toxin.

The invention also provides for an antibody which specifically binds a human TIE-2 ligand. The antibody may be monoclonal or polyclonal.

The invention further provides for a method of purifying a human TIE-2 ligand comprising:
 a) coupling at least one TIE-2 binding substrate to a solid matrix;
 b) incubating the substrate of a) with a cell lysate so that the substrate forms a complex with any human TIE-2 ligand in the cell lysate;
 c) washing the solid matrix; and
 d) eluting the human TIE-2 ligand from the coupled substrate.

The substrate may be any substance that specifically binds the human TIE-2 ligand. In one embodiment, the substrate is selected from the group consisting of anti-TIE-2 ligand antibody, TIE-2 receptor and TIE-2 receptorbody. The invention further provides for a receptorbody which specifically binds a human TIE-2 ligand, as well as a therapeutic composition comprising the receptorbody in a pharmaceutically acceptable vehicle, and a method of blocking blood vessel growth in a human comprising administering an effective amount of the therapeutic composition.

The invention also provides for a therapeutic composition comprising a human TIE-2 ligand or ligandbody in a pharmaceutically acceptable vehicle, as well as a method of promoting neovascularization in a patient comprising administering to the patient an effective amount of the therapeutic composition.

In addition, the present invention provides for a method for identifying a cell which expresses TIE-2 receptor which comprises contacting a cell with a detectably labeled TIE-2 ligand or ligandbody, under conditions permitting binding of the detectably labeled ligand to the TIE-2 receptor and determining whether the detectably labeled ligand is bound to the TIE-2 receptor, thereby identifying the cell as one which expresses TIE-2 receptor. The present invention also provides for a therapeutic composition comprising a TIE-2 ligand or ligandbody and a cytotoxic agent conjugated thereto. The cytotoxic agent may be a radioisotope or toxin.

The invention also provides a method of detecting expression of TIE-2 ligand by a cell which comprises obtaining mRNA from the cell, contacting the mRNA so obtained with a labelled nucleic acid molecule encoding a TIE-2 ligand, under hybridizing conditions, determining the presence of mRNA hybridized to the labelled molecule, and thereby detecting the expression of the TIE-2 ligand in the cell.

The invention further provides a method of detecting expression of a TIE-2 ligand in tissue sections which comprises contacting the tissue sections with a labelled nucleic acid molecule encoding a TIE-2 ligand, under hybridizing conditions, determining the presence of mRNA hybridized to the labelled molecule, and thereby detecting the expression of the TIE-2 ligand in tissue sections.

EXAMPLE 1

Identification of the Abae Cell Line as Reporter Cells for the TIE-2 Receptor

Adult BAE cells are registered in the European Cell Culture Repository, under ECACC#92010601. (See PNAS 75:2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2 \times 10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors, PMSF and aprotinin. Insoluble debris was removed from the cell lysates by centrifugation at 14,000×G for 10 minutes, at 4° C. and the supernatants were subjected to immune-precipitation with antisera specific for TIE-2 receptor, with or without the presence of blocking peptides added to ~20 µg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2-protein was visualized by incubation of the membrane with HRP-linked secondary antisera followed by treatment with ECL reagent (Amersham).

EXAMPLE 2

Cloning and Expression of TIE-2 Receptorbody for Afinity-Based Study of TIE-2 Ligand Interactions An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73:447–456 (1993).

Milligram quantities of TIE-2 RB were obtained by cloning the TIE-2 RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1–4 may be used. DNA encoding the TIE-2 RB vvas cloned as an Eco RI-NotI fragment into the baculovirus transfer plasmid pVL1393. Plasmid DNA purified by cesium chloride density gradient centrifugation was recombined into viral DNA by mixing 3 μg of plasmid DNA with 0.5 μg of Baculo-Gold DNA (Pharminigen), followed by introduction into liposomes using 30 μg Lipofectin (GIBCO-BRL). DNA-liposome mixtures were added to SF-21AE cells ($2 \times 10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, *Baculovirus Expression Vectors—A Laboratory Manual*. 1992, New York: W. H. Freeman) except that the agarose overlay contained 125 μg/mL X-gal (5-bromo-4-chloro-3-indolyl-β-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 μg/mL MTT (3-[4,5-dimethylthiazol-2-yl]2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptor body) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase ($\sim 2 \times 10^6$ cells per mL), concentrated by centrifugation, and infected with 5 plaque forming units of vTIE-2 Receptor Body per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions.

Culture medium from vTIE-2 Receptor Body-infected SF21AE cells were collected by centrifugation (500× g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 μm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TIE-2 RB were pooled and dialyzed versus PBS.

EXAMPLE 3

Demonstration That TIE-2 has a Critical Role in Development of the Vasculature

Given the absence of a known ligand for TIE-2 receptor, it was reasoned that it might be possible to gain insight into the function of TIE-2 by introduction of "excess" soluble TIE-2 receptor body (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extraembryonically-derived endothelial cells, which provide the major source for endothelial cells in the embryo, originate from accretions, of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intraembryonically-derived vascular elements.

Figure 1B:
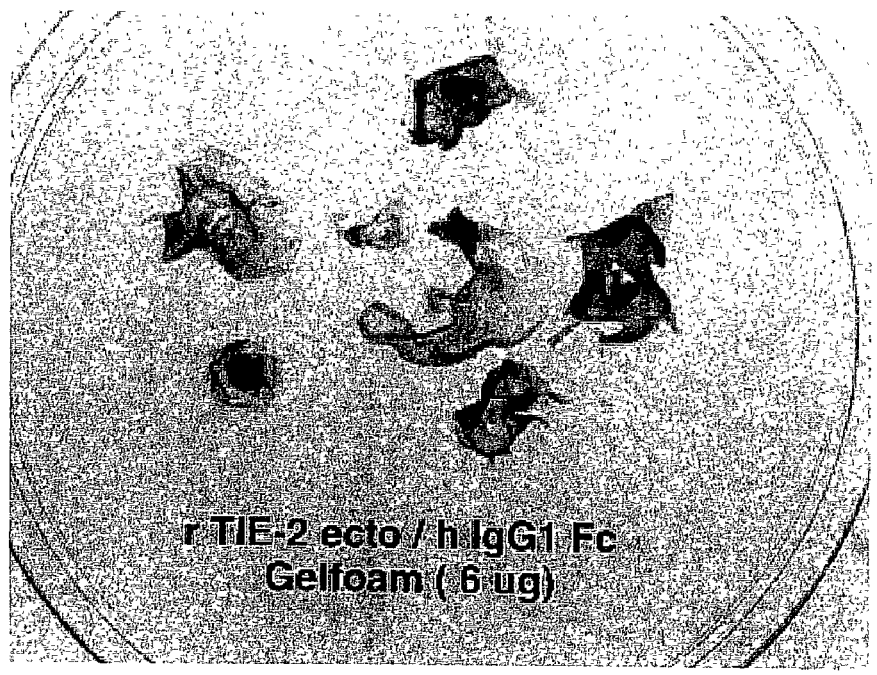

Newly fertilized chicken eggs obtained from Spafas, Inc. (Boston, Mass.) were incubated at 99.5° F., 55% RH. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al., Oncogene 8:3277–3288 (1993). Each Gelfoam piece absorbed approximately 6 μg of protein in 30 μl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1 (Maisonpierre et al., Oncogene 8:3277–3288 (1993). Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos, as shown in FIGS. 1A and 1B. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2–5 mm. in diameter, as compared with more than 10 mm. in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

Identification of a TIE-2-Specific Binding Activity in Conditioned Medium from the ras Oncongene-Transformed C2C12 Mouse Myoblast Cell Line Screening of ten-fold-concentrated cell-conditioned media (10× CCM) from various cell lines for the presence of soluble, TIE-2-specific binding activity (BIAcore; Pharmacia Biosensor, Piscataway, N.J.) revealed binding activity in serum-free medium from oncogenic-ras-transformed C2C12 cells (C2C12-ras), RAT 2-ras (which is a ras transformed fibroblast cell line), human glioblastoma T98G and the human neuroblastoma cell line known as SHEP-1.

The C2C12-ras 10× CCM originated from a stably-transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin-streptomycin supplemented with 10% fetal calf serum (FCS). Serum-free C2C12-ras 10× CCM was made by plating the cells at 60% confluence in a serum free defined media for 12 hours. (Zhan and Goldfarb, Mol. Cell. Biol. 6: 3541–3544 (1986)); Zhan, et al. Oncogene 1: 369–376 (1987)). The medium was discarded and replaced with fresh DMEM/Q/P-S for 24 hours. This medium was harvested and cells were refed fresh DMEM/Q/P-S, which was also harvested after a further 24 hours. These CCM were supplemented with the protease inhibitors PMSF (1 mM) and aprotinin (10 μg/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BIAcore analysis.

Binding activity of the 10× CCM was measured using biosensor technology (BIAcore; Pharmacia Biosensor, Piscataway, N.J.) which monitors biomolecular interactions in real-time via surface plasmon resonance. Purified TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 μg/mL, pH 4.5) and deactivation of unreacted sites with 1.0 M ethanolamine (pH 8.5). A negative control surface of the EHK-1 receptorbody was prepared in a similar manner.

The running buffer used in the system was HBS (10 mM Hepes, 3.4 mM edta, 150 mM NaCl, 0.005% P20 surfactant, pH 7.4). The 10× CCM samples were centrifuged for 15 min at 4 C and further clarified using a sterile, low protein-binding 0.45 μm filter (Millipore; Bedford, Mass.). Dextran (2 mg/ml) and P20 surfactant (0.005%) were added to each CCM sample. Aliquots of 40 μL were injected across the immobilized surface (either TIE-2 or EHK-1) at a flow rate of 5 μL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 12-μL pulse of 3 M $MgCl_2$.

The instrument noise level is 20 RU; therefore, any binding activity with a signal above 20 RU may be interpreted as a real interaction with the receptor. For C2C12-ras conditioned media, the binding activities were in the range 60–90 RU for the TIE-2 RB immobilized surface. For the same samples assayed on a EHK-1 RB immobilized surface, the measured activities were less than 35 RU. Specific binding to the TIE-2 receptorbody was evaluated by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 binding to the surface is two-thirds less than that measured in the absence of TIE-2. A repeat assay using >50× concentrated C2C12-ras CCM resulted in a four-fold enhancement over background of the TIE-2 specific binding signal.

EXAMPLE 5

C2C12-ras CCM Contains an Activity that Induces Tyrosine Phosphorylation of TIE-2 Receptor C2C12-ras 10× CCM was examined for its ability to induce tyrosine phosphorylation of TIE-2 in ABAE cells. Serum-starved ABAE cells were briefly incubated with C2C12-ras CCM, lysed and subjected to immunoprecipitation and Western analyses as described above. Stimulation of serum-starved ABAE cells with serum-free C2C12-ras 10× CCM was done as follows. The medium of ABAE cells starved as described above was removed and replaced with either defined medium or 10× CCM that had been pre-warmed to 37° C. After 10 minutes, the media were removed and the cells were twice rinsed on ice with an excess of chilled PBS supplemented with orthovanadate/NaF/benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras CCM stimulated at least a 100× increase in TIE-2 phosphorylation. This activity was almost totally depleted by pre-incubation of the C2C12-ras 10× CCM for 90 minutes at room temperature with 13 ug of TIE-2 RB coupled to protein G-Sepharose beads. Medium incubated with protein G Sepharose alone was not depleted of this phosphorylating activity.

EXAMPLE 6

Expression Cloning of TIE-2 Ligand

Figure 2:
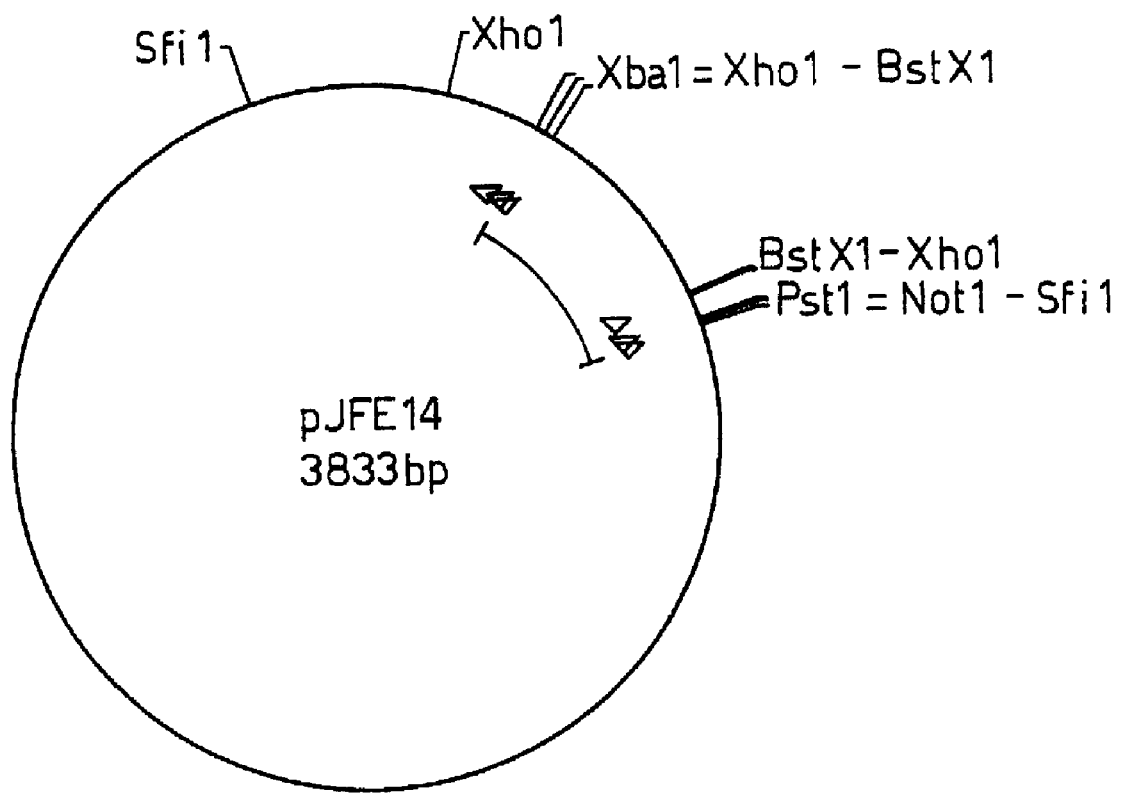
FIG. 2—Vector pJFE14.

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 50% $CO_2$. The mouse myoblast C2C12 ras cell line was cultured in Eagle's minimal essential medium (EMEM) with 10% FBS, (P/S) and 2 mM glutamine. Full length mouse TIE-2 ligand cDNA clones were obtained by screening a C2C12 ras cDNA library in the pJFE14 vector expressed in COS cells. This vector, as shown in FIG. 2, is a modified version of the vector $pSR_\alpha$ (Takebe, et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0 \times 10^6$ cells per 100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Two days after transfection the cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites. The screening was conducted by direct localization of staining using a TIE-2 receptorbody, which consisted of the extracellular domain of TIE-2 fused to the IgG1 constant region. This receptorbody was prepared as set forth in Example 2. A 100 mm dish of transfected, fixed and permeabilized COS cells was probed by incubating them for 30 min with TIE-2-RB. The cells were then washed twice with PBS and incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. For each stained cell, a small area of cells including the stained cell was scraped from the dish using a plastic pipette tip and plasmid DNA was then rescued and used to electroporate bacterial cells. Single bacterial colonies resulting from the electroporation were picked and plasmid DNA prepared from these colonies was used to transfect COS-7 cells which were probed for TIE-2 ligand expression as evidenced by binding to TIE-2 receptorbodies. This allowed identification of single clones coding for TIE-2 ligand. Confirmation of TIE-2 ligand expression was obtained by phosphorylation of the TIE-2 receptor using the method set forth in Example 5. A plasmid clone encoding the TIE-2 ligand was deposited with the ATCC on Oct. 7, 1994 and designated as "pJFE14 encoding TIE-2 ligand" under ATCC Accession No. 75910.

EXAMPLE 7

Isolation and Sequencing of Full Length cDNA Clone Encoding Human TIE-2 Ligand

Figure 3:
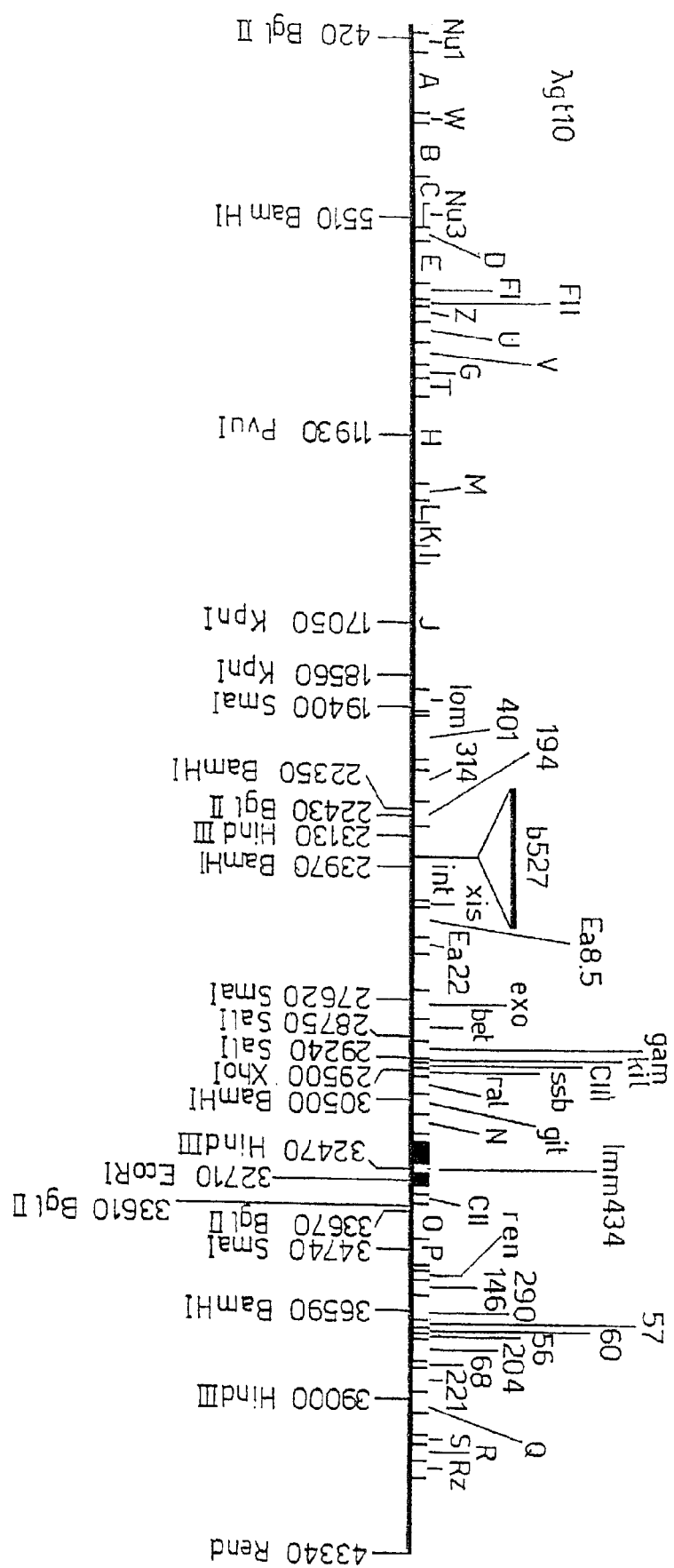
FIG. 3—Restriction map of λgt10.

A human fetal lung cDNA library in lambda gt-10 (see FIG. 3) was obtained from Clontech Laboratories, Inc. (Palo Alto, Calif.). Plaques were plated at a density of $1.25 \times 10^6/20 \times 20$ cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.).

Isolation of human tie-2 ligand clones was carried out as follows. A 2.2 kb XhoI fragment from the deposited tie-2 ligand clone (ATCC NO. 75910—see Example 6 above) was labeled by random priming to a specific activity of approximately $5 \times 10^8$ cpm/ng. Hybridization was carried out at 65° C. in hybridization solution containing 0.5 mg/ml salmon sperm DNA. The filters were washed at 65° C. in 2× SSC, 0.1% SDS and exposed to Kodak XAR-5 film overnight at −70° C. Positive phage were plaque purified. High titre phage lysates of pure phage were used for isolation of DNA via a Qiagen column using standard techniques (Qiagen, Inc., Chatsworth, Calif., 1995 catalog, page 36). Phage DNA was digested with EcoRI to release the cloned cDNA fragment for subsequent subcloning. A lambda phage vector containing human tie-2 ligand DNA was deposited with the ATCC on Oct. 26, 1994 under the designation λgt10 encoding htie-2 ligand 1 (ATCC Accession No. 75928). Phage DNA may be subjected directly to DNA sequence analysis by the dideoxy chain termination method (Sanger, et al., 1977, Proc. Natl. Acad. Sci. U.S.A. 74: 5463–5467).

Subcloning Human TIE-2 Ligand Into a Mammalian Expression Vector

The clone λgt10 encoding htie-2 ligand 1 contains an EcoRI site located 490 base pairs downstream from the start of the coding sequence for the human tie-2 ligand. The coding region may be excised using unique restriction sites upstream and downstream of the initiator and stop codons respectively. For example, an SpeI site, located 70 bp 5' to the initiator codon, and a Bpu1102i (also known as BlpI) site, located 265 bp 3' to the stop codon, may be used to excise the complete coding region. This may then be subcloned into the pJFE14 cloning vector, using the XbaI (compatible to the SpeI overhang) and the PstI sites (the PstI and Bpu1102i sites are both made blunt ended).

Sequencing of Human TIE-2 Ligand

The coding region from the clone λgt10 encoding htie-2 ligand 1 was sequenced using the ABI 373A DNA sequencer and Taq Dideoxy Terminator Cycle Sequencing Kit (Applied Biosystems, Inc., Foster City, Calif.). The nucleotide (SEQ ID NO: 1) and deduced amino acid sequence (SEQ ID NO: 2) of human TIE-2 ligand from the clone λgt10 encoding htie-2 ligand 1 is shown in FIGS. 4A–4D.

In addition, full length human TIE-2 ligand cDNA clones were obtained by screening a human glioblastoma T98G cDNA library in the pJFE14 vector. Clones encoding human tie-2 ligand were identified by DNA hybridization using a 2.2 kb XhoI fragment from the deposited tie-2 ligand clone (ATCC NO. 75910) as a probe (see Example 6 above). The coding region was sequenced using the ABI 373A DNA sequencer and Taq Dideoxy Terminator Cycle Sequencing Kit (Applied Biosystems, Inc., Foster City, Calif.). This sequence was nearly identical to that of clone λgt10 encoding htie-2 ligand 1. As shown in FIGS. 4A–4D (SEQ ID NO: 1), the clone λgt10 encoding htie-2 ligand 1 contains an additional glycine residue which is encoded by nucleotides 1114–1116. The coding sequence of the T98G clone does not contain this glycine residue but otherwise is identical to the coding sequence of the clone λgt10 encoding htie-2 ligand 1. FIGS. 5A–5D sets forth the nucleotide (SEQ ID NO: 3) and deduced amino acid sequence (SEQ ID NO: 4) of human TIE-2 ligand from the T98G clone.

EXAMPLE 8

Isolation and Sequencing of Second Full Length cDNA Clone A Encoding Human TIE-2 Ligand A human fetal lung cDNA library in lambda gt-10 (see FIG. 3) was obtained from Clontech Laboratories, Inc. (Palo Alto, Calif.). Plaques were plated at a density of 1.25× $10^6$/20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at low stringency (2×SSC, 55° C.) with probes made to the human tie 2 L-1 sequence. One of the duplicate filters was probed with a 5' probe, encoding amino acids 25–265 of human tie 2L-1 as set forth in FIGS. 4A–4D (SEQ ID NO: 2). The second duplicate filter was probed with a 3' probe, encoding amino acids 282–498 of human tie 2 L-1 sequence (see FIGS. 4A–4D (SEQ ID NO: 2). Both probes were hybridized at 55 C in hybridization solution containing 0.5 mg/ml salmon sperm DNA. Filters were washed in 2×SSC at 55° C. and exposed overnight to X-ray film. In addition, duplicate filters were also hybridized at normal stringency (2×SSC, 65° C.) to the full length coding probe of mouse tie2L (F3-15, XhoI insert). Three positive clones were picked that fulfilled the following criteria: i. hybridization had not been seen to the full length (mouse) probe at normal stringency, and ii. hybridization was seen at low stringency to both 5' and 3' probes. EcoRI digestion of phage DNA obtained from these clones indicated two independent clones with insert sizes of approximately 2.2 kb and approximately 1.8 kb. The 2.2 kb EcoRI insert was subcloned into the EcoRI sites of both pBluescript KS (Stratagene) and a mammalian expression vector suitable for use in COS cells. Two orientations were identified for the mammalian expression vector. The 2.2 kb insert in pBluescript KS was deposited with the ATCC on Dec. 9, 1994 and designated as pBluescript KS encoding human TIE 2 ligand 2. The start site of the TIE-2 ligand 2 coding sequence is approximately 355 base pairs downstream of the pBluescript EcoRI site.

COS-7 cells were transiently transfected with either the expression vector or control vector by the DEAE-dextran transfection protocol. Briefly, COS-7 cells were plated at a density of $1.0 \times 10^6$ cells per 100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of $1.0 \times 10^6$ cells per 100 mm plate. The cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites. The screening was conducted by direct localization of staining using a TIE-2 receptorbody, which consisted of the extracellular domain of TIE-2 fused to the IgG1 constant region. This receptorbody was prepared as set forth in Example 2. Transfected COS cells were probed by incubating them for 30 min with TIE-2-RB. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. Cells expressing one orientation of the clone, but not the other orientation, were seen to bind the TIE-2 receptor body.

One of skill in the art will readily see that the described methods may be used to further identify other related members of the TIE ligand family.

Sequencing of Second Human TIE-2 Ligand

The coding region from the clone pBluescript KS encoding human TIE-2 ligand 2 was sequenced using the ABI 373A DNA sequencer and Taq Dideoxy Terminator Cycle Sequencing Kit (Applied Biosystems, Inc., Foster City, Calif.). The nucleotide (SEQ ID NO: 5) and deduced amino acid sequence (SEQ ID NO: 6) of human TIE-2 ligand from the clone pBluescript KS encoding human TIE-2 ligand 2 is shown in FIGS. 6A–6D.

EXAMPLE 9

TIE-2 Ligand 2 is a Receptor Antagonist

Conditioned media from COS cells expressing either TIE-2 ligand 2 (TL2) or TIE-2 ligand 1 (TL1) were compared for their ability to activate TIE-2 receptors naturally present in a human endothelial cell line.

Lipofectamine reagent (GIBCO-BRL, Inc.) and recommended protocols were used to transfect COS-7 cells with either the pJFE14 expression vector alone, pJFE14 vector containing the human TIE-2 ligand 1 cDNA, or with a pMT21 expression vector (Kaufman, R. J., 1985, Proc. Natl. Acad. Sci. USA 82: 689–693) containing the human TIE-2 ligand 2 cDNA. COS media containing secreted ligands were harvested after three days and concentrated 20-fold by diafiltration (DIAFLO ultrafiltration membranes, Amicon, Inc.). The quantity of active TIE-2 ligand 1 and TIE-2 ligand 2 present in these media was determined and expressed as the amount (in resonance units, R.U.) of TIE-2 receptor specific binding activity measured by a BIAcore binding assay.

Figure 7:
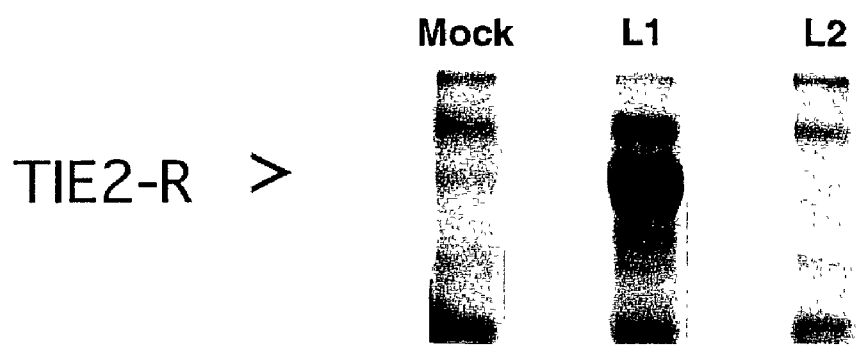
FIG. 7—Western blot showing activation of TIE-2 receptor by TIE-2 ligand 1 (Lane L1) but not by TIE-2 ligand 2 (Lane L2) or control (Mock).

Northern (RNA) analyses revealed significant levels of TIE-2 transcripts in HAEC (Human Aortic Endothelial Cell) human primary endothelial cells (Clonetics, Inc.). Therefore, these cells were used to examine whether TIE-2 receptor is tyrosine-phosphorylated when exposed to COS media containing the TIE-2 ligands. HAEC cells were maintained in a complete endothelial cell growth medium (Clonetics, Inc.) that contained 5% fetal bovine serum, soluble bovine brain extract, 10 ng/ml human EGF, 1 mg/ml hydrocortisone, 50 mg/ml gentamicin and 50 ng/ml amphotericin-B. Assessment of whether TL1 and TL2 could activate TIE-2 receptor in the HAEC cells was done as follows. Semi-confluent HAEC cells were serum-starved for two hours in high-glucose Dulbecco's MEM with added L-glutamine and penicillin-streptomycin at 37° C. followed by replacement of the starvation medium with ligand-containing conditioned COS media for 7 minutes at 37° C. in a 5% CO2 incubator. The cells were subsequently lysed and TIE-2 receptor protein was recovered by immunoprecipitation of the lysates with TIE-2 peptide antiserum, followed by Western blotting with antiphosphotyrosine antiserum, exactly as described in example 1. The results are shown in FIG. 7. Phosphotyrosine levels on the TIE-2 receptor (TIE2-R) were induced by treatment of HEAC cells with TIE-2 ligand 1 (Lane L1) but not by TIE-2 ligand 2 (Lane L2) conditioned COS media. MOCK is conditioned media from COS transfected with JFE14 empty vector.

Evidence that both TL1 and TL2 specifically bind to the TIE-2 receptor was demonstrated by using a BIAcore to assay the TIE-2 receptor specific binding activities in transfected COS media and by immunostaining of TL1- and TL2-expressing COS cells with TIE-2 receptorbodies.

Because TL2 did not activate the TIE-2 receptor, applicants set out to determine whether TL2 might be capable of serving as an antagonist of TL1 activity. HAEC phosphorylation assays were performed in which cells were first incubated with an "excess" of TL2, followed by addition of dilute TL1. It was reasoned that prior occupancy of TIE-2 receptor due to high levels of TL2 might prevent subsequent stimulation of the receptor following exposure to TL1 present at a limiting concentration.

Figure 8:
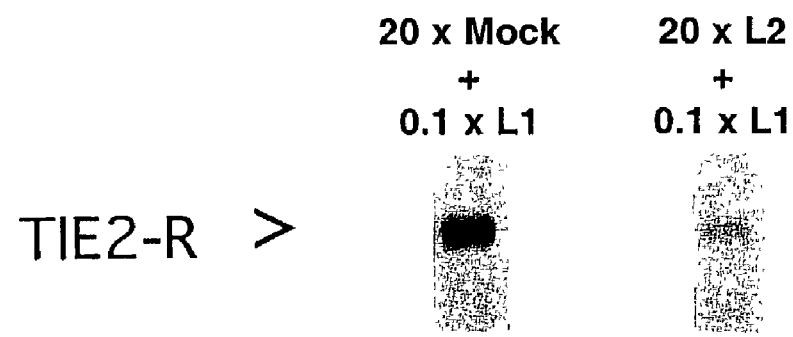
FIG. 8—Western blot showing that prior treatment of HAEC cells with excess TIE-2 ligand 2 (Lane 2) antagonizes the subsequent ability of dilute TIE-2 ligand 1 to activate the TIE-2 receptor (TIE2-R) as compared with prior treatment of HAEC cells with MOCK medium (Lane 1).
Figure 9A:
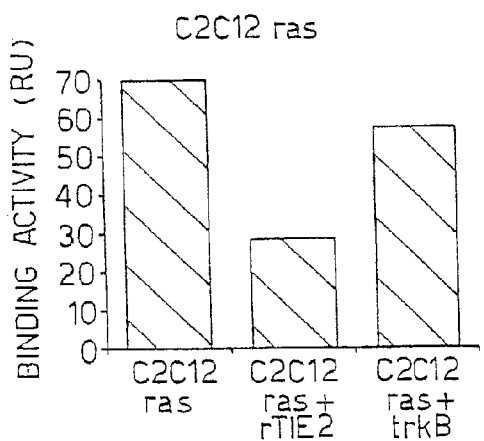
FIGS. 9A–9D—Histogram representation of binding to rat TIE2 IgG immobilized surface by TIE2 ligand in C2C12 ras (FIG. 9A), Rat2 ras (FIG. 9B), SHEP (FIG. 9C), and T98G (FIG. 9D) concentrated (10×) conditioned medium. Rat TIE2 (rTIE2) specific binding is demonstrated by the significant reduction in the binding activity in the presence of 25 µg/ml soluble rat TIE2 RB as compared to a minor reduction in the presence of soluble trkB RB.
Figure 9B:
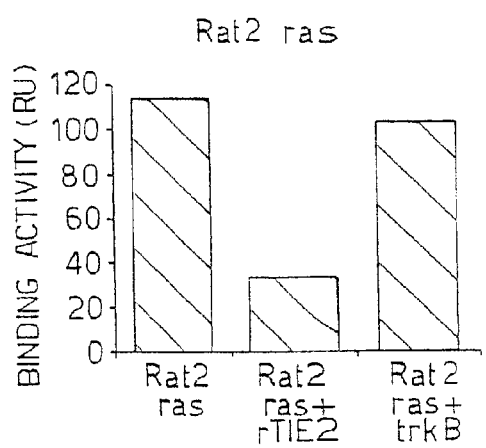
Figure 9C:
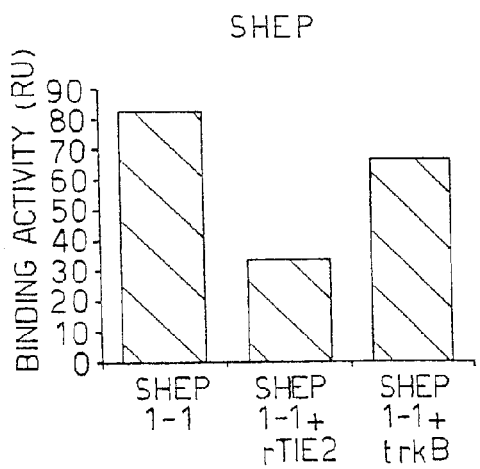
Figure 9D:
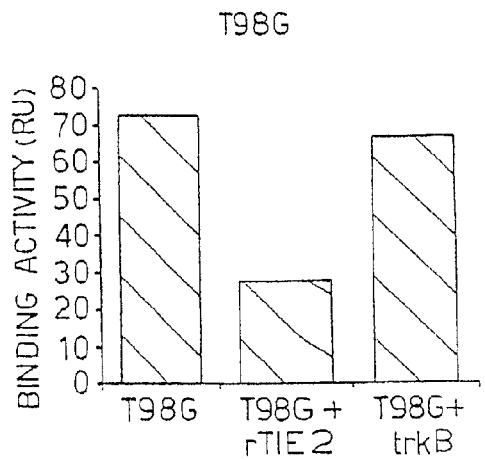
Figure 10A:
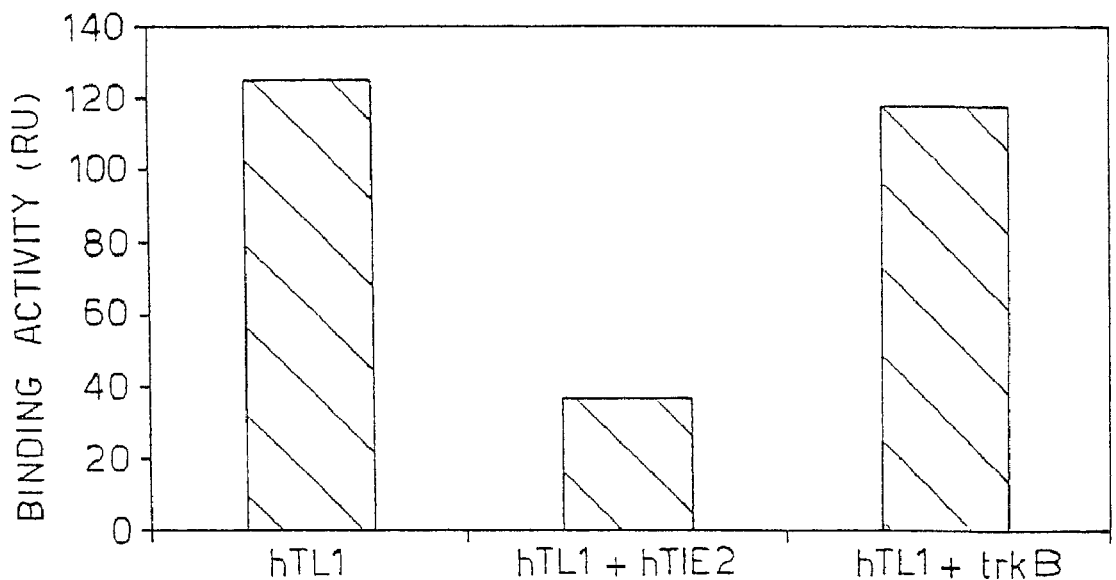
FIGS. 10A–10B—Binding of recombinant human TJE-2 ligand 1 (hTL1) (FIG. 10A) and human TIE-2 ligand 2 (hTL2) (FIG. 10B), in cos cell supernatants, to a human TIE-2 RB immobilized surface. Human TIE-2-specific binding was determined by incubating the samples with 25 µg/ml of either soluble human TIE2 RB or trkB RB; significant reduction in the binding activity is observed only for the samples incubated with human TIE2 RB.
Figure 10B:
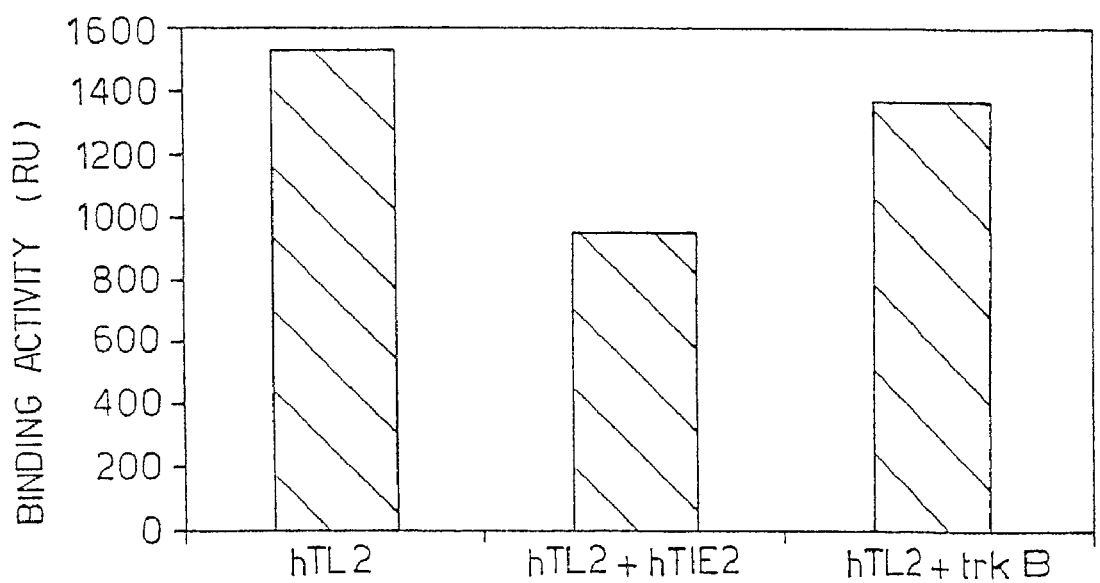

Semi-confluent HAEC cells were serum-starved as described above and then incubated for 3 min., at 37° C. with 1–2 ml. of 20× COS/JFE14-TL2 conditioned medium. Control plates were treated with 20× COS/JFE14-only medium (MOCK). The plates were removed from the incubator and various dilutions of COS/JFE14-TL1 medium were then added, followed by further incubation of the plates for 5–7 min. at 37° C. Cells were subsequently rinsed, lysed and TIE-2-specific tyrosine phosphorylation in the lysates was examined by receptor immunoprecipitation and Western blotting, as described above. TL1 dilutions were made using 20× COS/JFE14-TL1 medium diluted to 2×, 0.5×, 0.1×, or 0.02× by addition of 20× COS/JFE14-alone medium. An assay of the initial 20× TL1 and 20× TL2 COS media using BIAcore biosensor technology indicated that they contained similar amounts of TIE-2-specific binding activities, i.e., 445 R.U. and 511 R.U. for TL1 and TL2, respectively. The results of the antiphosphotyrosine Western blot, shown in FIG. 8, indicate that when compared to prior treatment of HAEC cells with MOCK medium (lane 1), prior treatment of HAEC cells with excess TIE-2 ligand 2 (lane 2) antagonizes the subsequent ability of dilute TIE-2 ligand 1 to activate the TIE-2 receptor (TIE2-R).

These data indicate that, unlike TL1, TL2 was not able to stimulate TIE-2 receptor kinase activity in HAEC cells. Furthermore, pre-incubation of the endothelial cells with high concentrations of TL2 followed by addition of TL1 blocked the ability of TL1 to stimulate the TIE-2 receptor, indicating that TL2 is a TIE-2 receptor antagonist.

EXAMPLE 10

Identification of TIE-2-Specific Binding Activity in Conditioned Medium and Cos Cell Supernatants Binding activity of 10× CCM from the cell lines C2C12 ras, Rat2 ras, SHEP, and T98G, or cos cell supernatants after transfection with either human TIE-2 ligand 1 (hTL1) or human TIE-2 ligand 2 (hTL2) was measured using biosensor technology (BIAcore; Pharmacia Biosensor, Piscataway, N.J.) which monitors biomolecular interactions in real-time via surface plasmon resonance (SPR). Purified rat or human TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0 M ethanolamine (pH 8.5). In general, 9000–10000 RU of each receptorbody was coupled to the sensor chip.

The running buffer used in the system was HBS (10 mM Hepes, 150 mM NaCl, 0.005% P20 surfactant, pH 7.4). The samples were centrifuged for 15 min at 4° C. and further clarified using a sterile, low protein-binding 0.45 µm filter (Millipore; Bedford, Mass.). Dextran (2 mg/ml) and P20 surfactant (0.005%) were added to each sample. Aliquots of 40 µL were injected across the immobilized surface (either rat or human TIE2) at a flow rate of 5 µL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 15-µL pulse of 3 M $MgCl_2$.

The CCM samples (C2C12 ras, Rat2 ras, SHEP, T98G) were tested on the rat TIE2 RB immobilized surface, while the recombinant hTL1 and hTL2 were tested on the human TIE2 RB immobilized surface. In each case, specific binding to the TIE-2 receptorbody was evaluated by incubating the samples with 25 μg/ml of either soluble TIE-2 (rat or human) RB or trkB RB prior to assaying the binding activity. As shown in FIGS. 9A–9D and FIGS. 10A and 10B, the addition of soluble trkB RB causes a slight decrease in the TIE-2 binding activity, while the addition of soluble TIE-2 RB significantly reduces the binding activity as compared to that measured in the absence of TIE-2 RB.

EXAMPLE 11

TIE-2 RB Specifically Blocks Activation of the TIE-2 Receptor by TIE-2 Ligand 1

The applicants sought to determine whether soluble TIE-2 RB can serve as a competitive inhibitor to block activation of TIE-2 receptor by TIE-2 ligand 1 (TL1). To do this, TL1-containing COS media were preincubated with either TIE2- or TrkB-RB and then compared for their ability to activate TIE-2 receptors naturally present in a human endothelial cell line.

Conditioned COS media were generated from COS-7 cells transfected with either the pJFE14 expression vector alone (MOCK), or pJFE14 vector containing the human TIE-2 ligand 1 cDNA (TL1) and harvested as described in Example 9 hereinabove, with the exception that the media were sterile filtered but not concentrated. The quantity of TL1 was determined and expressed as the amount (in resonance units, R.U.) of TIE-2 receptor-specific binding activity measured by BIAcore binding assay.

Figure 11:
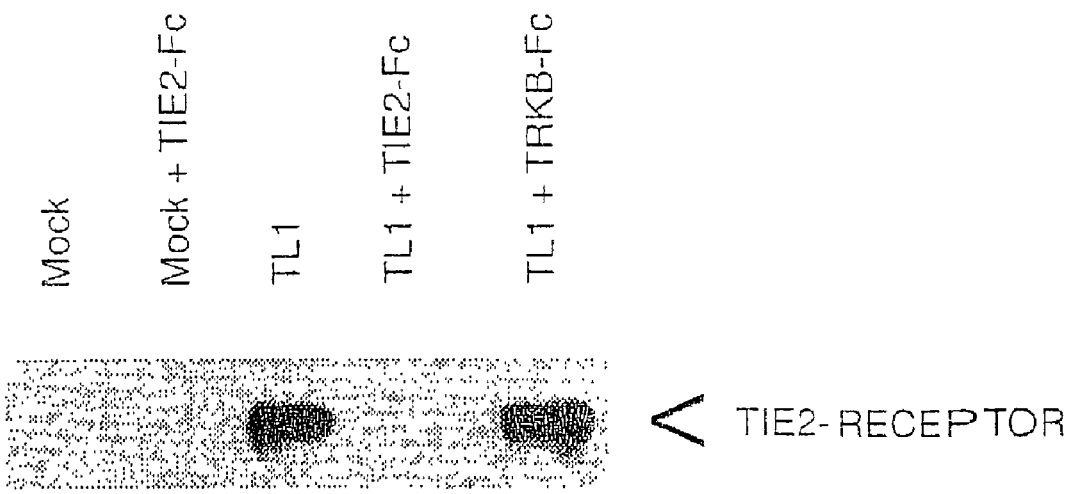
FIG. 11—Western blot showing that TIE-2 receptorbody (denoted TIE-2 RB or, as here, TIE2-Fc) blocks the activation of TIE-2 receptors by TIE-2 ligand 1 (TL1) in HUVEC cells, whereas an unrelated receptorbody (TRKB-Fc) does not block this activation.

Northern (RNA) analyses revealed significant levels of TIE-2 transcripts in HUVEC (Human Umbilical Vein Endothelial Cell) human primary endothelial cells (Clonetics, Inc.). Therefore, these cells were used to examine whether TIE-2 receptor can be tyrosine-phosphorylated when exposed in the presence of TIE2- or TrkB-RBs to COS media containing TL1. HUVEC cells were maintained at 37° C., 5% CO2 in a complete endothelial cell growth medium (Clonetics, Inc.) that contained 5% fetal bovine serum, soluble bovine brain extract with 10 ug/ml heparin, 10 ng/ml human EGF, 1 ug/ml hydrocortisone, 50 ug/ml gentamicin and 50 ng/ml amphotericin-B. Assessment of whether TL1 could activate TIE-2 receptor in the HUVEC cells was done as follows. Confluent dishes of HUVEC cells were serum-starved for two-to-four hours in low-glucose Dulbecco's MEM at 37° C., 5% CO2, followed by 10 minute incubation in starvation medium that included 0.1 mM sodium orthovanadate, a potent inhibitor of phosphotyrosine phosphatases. Meanwhile, conditioned COS media were preincubated 30 min. at room temperature with either TIE2- or TrkB-RB added to 50 ug/ml. The starvation medium was then removed from the HUVEC dishes and incubated with the RB-containing COS media for 7 minutes at 37° C. HUVEC cells were subsequently lysed and TIE-2 receptor protein was recovered by immunoprecipitation with TIE-2 peptide antiserum, followed by Western blotting with an anti-phosphotyrosine antibody, as described in Example 1. The results are shown in FIG. 11. Phosphotyrosine levels on the TIE-2 receptor were induced by treatment of HUVEC cells with TIE-2 ligand 1 (TL1) relative to that seen with control medium (MOCK) and this induction is specifically blocked by prior incubation with TIE2-RB (TIE2-Fc) but not by incubation with TrkB-RB (TrkB-Fc). These data indicate that soluble TIE-2 RB can serve as a selective inhibitor to block activation of TIE-2 receptor by TIE-2 ligand 1.

EXAMPLE 12

Construction of TIE-2 Ligandbodies

An expression construct was created that would yield a secreted protein consisting of the entire coding sequence of human TIE-2 ligand (TL1) or TIE-2 ligand 2 (TL2) fused to the human immunoglobulin gamma-1 constant region (IgG1 Fc). These fusion proteins are called TIE-2 "ligandbodies" (TL1-Fc or TL2-Fc). The Fc portion of TL1-Fc and TL2-Fc was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding full-length TL1 or TL2 and from the human IgG1 Fc plasmid were ligated on either side of a short PCR-derived fragment that was designed so as to fuse, in-frame, TL1 or TL2 with human IgG1 Fc protein-coding sequences.

Milligram quantities of TL2-Fc were obtained by cloning the TL2-Fc DNA fragment into the pVL1393 baculovirus vector and subsequently infecting the Spodoptera frugiperda SF-21AE insect cell line. Alternatively, the cell line SF-9 (ATCC Accession No. CRL-1711) or the cell line BTI-TN-5b1–4 may be used. DNA encoding the TL2-Fc was cloned as an Eco RI-NotI fragment into the baculovirus transfer plasmid pVL1393. Plasmid DNA was recombined into viral DNA by mixing 3 mg of plasmid DNA with 0.5 mg of Baculo-Gold DNA (Pharminigen), followed by introduction into liposomes using 30 mg Lipofectin (GIBCO-BRL). DNA-liposome mixtures were added to SF-21AE cells (2×106 cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors—A Laboratory Manual. 1992, New York: W. H. Freeman) except that the agarose overlay contained 125 mg/mL X-gal (5-bromo-4-chloro-3-indolyl-b- D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 mg/mL MTT (3-[4,5-dimethylthiazol-2-yl] 2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTL2-Fc Clone #7) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10 6 cells per mL), concentrated by centrifugation, and infected with 5 plaque forming units of vTL2-Fc per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions.

Culture medium from vTL2-Fc-infected SF21AE cells were collected by centrifugation (500× g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 mm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TL2-Fc were pooled and dialyzed versus PBS.

DEPOSITS

The following have been deposited with the American Type Culture Collection, 10801 University Boulevard, Manassas, Va. 20110-2209 in accordance with the Budapest Treaty. A plasmid clone encoding a TIE-2 ligand was deposited with the ATCC on Oct. 7, 1994 and designated as "pJFE14 encoding TIE-2 ligand" under ATCC Accession No. 75910. Recombinant Autographa californica baculovirus encoding TIE-2 receptor body was deposited with the ATCC on Oct. 7, 1994 and designated as "vTIE-2 receptor body" under ATCC Accession No. VR2484. A lambda phage vector containing human tie-2 ligand DNA was deposited with the ATCC on Oct. 26, 1994 and designated as lgt10 encoding htie-2 ligand 1 under ATCC Accession No. 75928. A plasmid clone encoding a second TIE-2 ligand was deposited with the ATCC on Dec. 9, 1994 and designated as "pBluescript KS encoding human TIE 2 ligand 2" under ATCC Accession No. 75963.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. An isolated antibody which specifically binds a ligand wherein the ligand consists of the amino acid sequence of SEQ ID NO: 2.

2. The antibody of claim 1 which is a monoclonal antibody.

3. A composition comprising the antibody of claim 1 and a carrier.

4. The antibody of claim 1 which is a chimeric antibody.

5. The antibody of claim 2 which is a chimeric antibody.

6. A composition comprising the antibody of claim 2 and a carrier.

7. The antibody of claim 1 which is a polyclonal antibody.

8. An isolated antibody fragment which specifically binds a ligand wherein the ligand consists of the amino acid sequence of SEQ ID NO:2.

9. The antibody fragment of claim 8, wherein the antibody fragment is an F(ab')$_2$ fragment or an Fab' fragment.

10. The antibody fragment of claim 8 comprising a fragment of a monoclonal antibody.

11. The antibody fragment of claim 10, wherein the antibody fragment is an F(ab')$_2$ fragment or an Fab' fragment.

* * * * *

SEQUENCE LISTING

```
<160> NUMBER OF SEQ ID NOS: 6

<210> SEQ ID NO 1
<211> LENGTH: 2149
<212> TYPE: DNA
<213> ORGANISM: Artificial Sequence
<220> FEATURE:
<223> OTHER INFORMATION: Unknown Organism
<220> FEATURE:
<221> NAME/KEY: CDS
<222> LOCATION: (310)...(1806)

<400> SEQUENCE: 1
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgaggggga aagagtcaaa caaacaagca gttttacctg aaataaagaa     240
ctagttttag aggtcagaag aaaggagcaa gttttgcgag aggcacggaa ggagtgtgct     300 ggcagtaca atg aca gtt ttc ctt tcc ttt gct ttc ctc gct gcc att        348
          Met Thr Val Phe Leu Ser Phe Ala Phe Leu Ala Ala Ile
            1               5                  10 ctg act cac ata ggg tgc agc aat cag cgc cga agt cca gaa aac agt       396
Leu Thr His Ile Gly Cys Ser Asn Gln Arg Arg Ser Pro Glu Asn Ser
     15                  20                  25 ggg aga aga tat aac cgg att caa cat ggg caa tgt gcc tac act ttc       444
Gly Arg Arg Tyr Asn Arg Ile Gln His Gly Gln Cys Ala Tyr Thr Phe
 30                  35                  40                  45 att ctt cca gaa cac gat ggc aac tgt cgt gag agt acg aca gac cag       492
Ile Leu Pro Glu His Asp Gly Asn Cys Arg Glu Ser Thr Thr Asp Gln
                 50                  55                  60 tac aac aca aac gct ctg cag aga gat gct cca cac gtg gaa ccg gat       540
Tyr Asn Thr Asn Ala Leu Gln Arg Asp Ala Pro His Val Glu Pro Asp
             65                  70                  75 ttc tct tcc cag aaa ctt caa cat ctg gaa cat gtg atg gaa aat tat       588
Phe Ser Ser Gln Lys Leu Gln His Leu Glu His Val Met Glu Asn Tyr
         80                  85                  90
```

| | | |
|---|---|---|
| act cag tgg ctg caa aaa ctt gag aat tac att gtg gaa aac atg aag<br>Thr Gln Trp Leu Gln Lys Leu Glu Asn Tyr Ile Val Glu Asn Met Lys<br>    95                          100                      105 | 636 |
| tcg gag atg gcc cag ata cag cag aat gca gtt cag aac cac acg gct<br>Ser Glu Met Ala Gln Ile Gln Gln Asn Ala Val Gln Asn His Thr Ala<br>110                       115                      120                  125 | 684 |
| acc atg ctg gag ata gga acc agc ctc ctc tct cag act gca gag cag<br>Thr Met Leu Glu Ile Gly Thr Ser Leu Leu Ser Gln Thr Ala Glu Gln<br>                        130                      135                  140 | 732 |
| acc aga aag ctg aca gat gtt gag acc cag gta cta aat caa act tct<br>Thr Arg Lys Leu Thr Asp Val Glu Thr Gln Val Leu Asn Gln Thr Ser<br>          145                      150                      155 | 780 |
| cga ctt gag ata cag ctg ctg gag aat tca tta tcc acc tac aag cta<br>Arg Leu Glu Ile Gln Leu Leu Glu Asn Ser Leu Ser Thr Tyr Lys Leu<br>                160                      165                      170 | 828 |
| gag aag caa ctt ctt caa cag aca aat gaa atc ttg aag atc cat gaa<br>Glu Lys Gln Leu Leu Gln Gln Thr Asn Glu Ile Leu Lys Ile His Glu<br>        175                      180                      185 | 876 |
| aaa aac agt tta tta gaa cat aaa atc tta gaa atg gaa gga aaa cac<br>Lys Asn Ser Leu Leu Glu His Lys Ile Leu Glu Met Glu Gly Lys His<br>190                       195                      200                  205 | 924 |
| aag gaa gag ttg gac acc tta aag gaa gag aaa gag aac ctt caa ggc<br>Lys Glu Glu Leu Asp Thr Leu Lys Glu Glu Lys Glu Asn Leu Gln Gly<br>                      210                      215                  220 | 972 |
| ttg gtt act cgt caa aca tat ata atc cag gag ctg gaa aag caa tta<br>Leu Val Thr Arg Gln Thr Tyr Ile Ile Gln Glu Leu Glu Lys Gln Leu<br>                225                      230                      235 | 1020 |
| aac aga gct acc acc aac aac agt gtc ctt cag aag cag caa ctg gag<br>Asn Arg Ala Thr Thr Asn Asn Ser Val Leu Gln Lys Gln Gln Leu Glu<br>              240                      245                      250 | 1068 |
| ctg atg gac aca gtc cac aac ctt gtc aat ctt tgc act aaa gaa ggt<br>Leu Met Asp Thr Val His Asn Leu Val Asn Leu Cys Thr Lys Glu Gly<br>        255                      260                      265 | 1116 |
| gtt tta cta aag gga gga aaa aga gag gaa gag aaa cca ttt aga gac<br>Val Leu Leu Lys Gly Gly Lys Arg Glu Glu Glu Lys Pro Phe Arg Asp<br>270                       275                      280                  285 | 1164 |
| tgt gca gat gta tat caa gct ggt ttt aat aaa agt gga atc tac act<br>Cys Ala Asp Val Tyr Gln Ala Gly Phe Asn Lys Ser Gly Ile Tyr Thr<br>                290                      295                      300 | 1212 |
| att tat att aat aat atg cca gaa ccc aaa aag gtg ttt tgc aat atg<br>Ile Tyr Ile Asn Asn Met Pro Glu Pro Lys Lys Val Phe Cys Asn Met<br>                    305                      310                      315 | 1260 |
| gat gtc aat ggg gga ggt tgg act gta ata caa cat cgt gaa gat gca<br>Asp Val Asn Gly Gly Gly Trp Thr Val Ile Gln His Arg Glu Asp Ala<br>        320                      325                      330 | 1308 |
| agt cta gat ttc caa aga ggc tgg aag gaa tat aaa atg ggt ttt gga<br>Ser Leu Asp Phe Gln Arg Gly Trp Lys Glu Tyr Lys Met Gly Phe Gly<br>335                       340                      345 | 1356 |
| aat ccc tcc ggt gaa tat tgg ctg ggg aat gag ttt att ttt gcc att<br>Asn Pro Ser Gly Glu Tyr Trp Leu Gly Asn Glu Phe Ile Phe Ala Ile<br>350                       355                      360                  365 | 1404 |
| acc agt cag agg cag tac atg cta aga att gag tta atg gac tgg gaa<br>Thr Ser Gln Arg Gln Tyr Met Leu Arg Ile Glu Leu Met Asp Trp Glu<br>                    370                      375                      380 | 1452 |
| ggg aac cga gcc tat tca cag tat gac aga ttc cac ata gga aat gaa<br>Gly Asn Arg Ala Tyr Ser Gln Tyr Asp Arg Phe His Ile Gly Asn Glu<br>        385                      390                      395 | 1500 |
| aag caa aac tat agg ttg tat tta aaa ggt cac act ggg aca gca gga<br>Lys Gln Asn Tyr Arg Leu Tyr Leu Lys Gly His Thr Gly Thr Ala Gly<br>400                       405                      410 | 1548 |

```
aaa cag agc agc ctg atc tta cac ggt gct gat ttc agc act aaa gat    1596
Lys Gln Ser Ser Leu Ile Leu His Gly Ala Asp Phe Ser Thr Lys Asp
    415                 420                 425 gct gat aat gac aac tgt atg tgc aaa tgt gcc ctc atg tta aca gga    1644
Ala Asp Asn Asp Asn Cys Met Cys Lys Cys Ala Leu Met Leu Thr Gly
430                 435                 440                 445 gga tgg tgg ttt gat gct tgt ggc ccc tcc aat cta aat gga atg ttc    1692
Gly Trp Trp Phe Asp Ala Cys Gly Pro Ser Asn Leu Asn Gly Met Phe
                    450                 455                 460 tat act gcg gga caa aac cat gga aaa ctg aat ggg ata aag tgg cac    1740
Tyr Thr Ala Gly Gln Asn His Gly Lys Leu Asn Gly Ile Lys Trp His
                465                 470                 475 tac ttc aaa ggg ccc agt tac tcc tta cgt tcc aca act atg atg att    1788
Tyr Phe Lys Gly Pro Ser Tyr Ser Leu Arg Ser Thr Thr Met Met Ile
            480                 485                 490 cga cct tta gat ttt tga aagcgcaatg tcagaagcga ttatgaaagc           1836
Arg Pro Leu Asp Phe
        495 aacaaagaaa tccggagaag ctgccaggtg agaaactgtt tgaaaacttc agaagcaaac  1896 aatattgtct cccttccagc aataagtggt agttatgtga agtcaccaag gttcttgacc  1956 gtgaatctgg agccgtttga gttcacaaga gtctctactt ggggtgacag tgctcacgtg  2016 gctcgactat agaaaactcc actgactgtc gggctttaaa aagggaagaa actgctgagc  2076 ttgctgtgct tcaaactact actggacctt attttggaac tatggtagcc agatgataaa  2136 tatggttaat ttc                                                    2149

<210> SEQ ID NO 2
<211> LENGTH: 498
<212> TYPE: PRT
<213> ORGANISM: Artificial Sequence
<220> FEATURE:
<223> OTHER INFORMATION: Unknown Organism

<400> SEQUENCE: 2

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Thr Thr Asp Gln Tyr Asn Thr
        50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175
```

```
Leu Leu Gln Gln Thr Asn Glu Ile Leu Lys Ile His Glu Lys Asn Ser
            180                 185                 190
Leu Leu Glu His Lys Ile Leu Glu Met Glu Gly Lys His Lys Glu Glu
        195                 200                 205
Leu Asp Thr Leu Lys Glu Glu Lys Glu Asn Leu Gln Gly Leu Val Thr
    210                 215                 220
Arg Gln Thr Tyr Ile Ile Gln Glu Leu Glu Lys Gln Leu Asn Arg Ala
225                 230                 235                 240
Thr Thr Asn Asn Ser Val Leu Gln Lys Gln Gln Leu Glu Leu Met Asp
                245                 250                 255
Thr Val His Asn Leu Val Asn Leu Cys Thr Lys Glu Gly Val Leu Leu
            260                 265                 270
Lys Gly Gly Lys Arg Glu Glu Lys Pro Phe Arg Asp Cys Ala Asp
        275                 280                 285
Val Tyr Gln Ala Gly Phe Asn Lys Ser Gly Ile Tyr Thr Ile Tyr Ile
    290                 295                 300
Asn Asn Met Pro Glu Pro Lys Lys Val Phe Cys Asn Met Asp Val Asn
305                 310                 315                 320
Gly Gly Gly Trp Thr Val Ile Gln His Arg Glu Asp Ala Ser Leu Asp
                325                 330                 335
Phe Gln Arg Gly Trp Lys Glu Tyr Lys Met Gly Phe Gly Asn Pro Ser
            340                 345                 350
Gly Glu Tyr Trp Leu Gly Asn Glu Phe Ile Phe Ala Ile Thr Ser Gln
        355                 360                 365
Arg Gln Tyr Met Leu Arg Ile Glu Leu Met Asp Trp Glu Gly Asn Arg
    370                 375                 380
Ala Tyr Ser Gln Tyr Asp Arg Phe His Ile Gly Asn Glu Lys Gln Asn
385                 390                 395                 400
Tyr Arg Leu Tyr Leu Lys Gly His Thr Gly Thr Ala Gly Lys Gln Ser
                405                 410                 415
Ser Leu Ile Leu His Gly Ala Asp Phe Ser Thr Lys Asp Ala Asp Asn
            420                 425                 430
Asp Asn Cys Met Cys Lys Cys Ala Leu Met Leu Thr Gly Gly Trp Trp
        435                 440                 445
Phe Asp Ala Cys Gly Pro Ser Asn Leu Asn Gly Met Phe Tyr Thr Ala
    450                 455                 460
Gly Gln Asn His Gly Lys Leu Asn Gly Ile Lys Trp His Tyr Phe Lys
465                 470                 475                 480
Gly Pro Ser Tyr Ser Leu Arg Ser Thr Thr Met Met Ile Arg Pro Leu
                485                 490                 495
Asp Phe

<210> SEQ ID NO 3
<211> LENGTH: 2146
<212> TYPE: DNA
<213> ORGANISM: Artificial Sequence
<220> FEATURE:
<223> OTHER INFORMATION: Unknown Organism
<220> FEATURE:
<221> NAME/KEY: CDS
<222> LOCATION: (310)...(1803)

<400> SEQUENCE: 3
cagctgactc aggcaggctc catgctgaac ggtcacacag agaggaaaca ataaatctca     60
gctactatgc aataaatatc tcaagtttta acgaagaaaa acatcattgc agtgaaataa    120
```

-continued

```
aaaatttta aattttagaa caaagctaac aaatggctag ttttctatga ttcttcttca      180
aacgctttct ttgagggga aagagtcaaa caaacaagca gttttacctg aaataaagaa      240
ctagttttag aggtcagaag aaaggagcaa gttttgcgag aggcacggaa ggagtgtgct      300 ggcagtaca atg aca gtt ttc ctt tcc ttt gct ttc ctc gct gcc att         348
         Met Thr Val Phe Leu Ser Phe Ala Phe Leu Ala Ala Ile
           1               5                  10 ctg act cac ata ggg tgc agc aat cag cgc cga agt cca gaa aac agt       396
Leu Thr His Ile Gly Cys Ser Asn Gln Arg Arg Ser Pro Glu Asn Ser
         15                  20                  25 ggg aga aga tat aac cgg att caa cat ggg caa tgt gcc tac act ttc       444
Gly Arg Arg Tyr Asn Arg Ile Gln His Gly Gln Cys Ala Tyr Thr Phe
 30                  35                  40                  45 att ctt cca gaa cac gat ggc aac tgt cgt gag agt acg aca gac cag       492
Ile Leu Pro Glu His Asp Gly Asn Cys Arg Glu Ser Thr Thr Asp Gln
                 50                  55                  60 tac aac aca aac gct ctg cag aga gat gct cca cac gtg gaa ccg gat       540
Tyr Asn Thr Asn Ala Leu Gln Arg Asp Ala Pro His Val Glu Pro Asp
             65                  70                  75 ttc tct tcc cag aaa ctt caa cat ctg gaa cat gtg atg gaa aat tat       588
Phe Ser Ser Gln Lys Leu Gln His Leu Glu His Val Met Glu Asn Tyr
         80                  85                  90 act cag tgg ctg caa aaa ctt gag aat tac att gtg gaa aac atg aag       636
Thr Gln Trp Leu Gln Lys Leu Glu Asn Tyr Ile Val Glu Asn Met Lys
     95                 100                 105 tcg gag atg gcc cag ata cag cag aat gca gtt cag aac cac acg gct       684
Ser Glu Met Ala Gln Ile Gln Gln Asn Ala Val Gln Asn His Thr Ala
110                 115                 120                 125 acc atg ctg gag ata gga acc agc ctc ctc tct cag act gca gag cag       732
Thr Met Leu Glu Ile Gly Thr Ser Leu Leu Ser Gln Thr Ala Glu Gln
                130                 135                 140 acc aga aag ctg aca gat gtt gag acc cag gta cta aat caa act tct       780
Thr Arg Lys Leu Thr Asp Val Glu Thr Gln Val Leu Asn Gln Thr Ser
            145                 150                 155 cga ctt gag ata cag ctg ctg gag aat tca tta tcc acc tac aag cta       828
Arg Leu Glu Ile Gln Leu Leu Glu Asn Ser Leu Ser Thr Tyr Lys Leu
        160                 165                 170 gag aag caa ctt ctt caa cag aca aat gaa atc ttg aag atc cat gaa       876
Glu Lys Gln Leu Leu Gln Gln Thr Asn Glu Ile Leu Lys Ile His Glu
    175                 180                 185 aaa aac agt tta tta gaa cat aaa atc tta gaa atg gaa gga aaa cac       924
Lys Asn Ser Leu Leu Glu His Lys Ile Leu Glu Met Glu Gly Lys His
190                 195                 200                 205 aag gaa gag ttg gac acc tta aag gaa gag aaa gag aac ctt caa ggc       972
Lys Glu Glu Leu Asp Thr Leu Lys Glu Glu Lys Glu Asn Leu Gln Gly
                210                 215                 220 ttg gtt act cgt caa aca tat ata atc cag gag ctg gaa aag caa tta      1020
Leu Val Thr Arg Gln Thr Tyr Ile Ile Gln Glu Leu Glu Lys Gln Leu
            225                 230                 235 aac aga gct acc acc aac aac agt gtc ctt cag aag cag caa ctg gag      1068
Asn Arg Ala Thr Thr Asn Asn Ser Val Leu Gln Lys Gln Gln Leu Glu
        240                 245                 250 ctg atg gac aca gtc cac aac ctt gtc aat ctt tgc act aaa gaa gtt      1116
Leu Met Asp Thr Val His Asn Leu Val Asn Leu Cys Thr Lys Glu Val
    255                 260                 265 tta cta aag gga gga aaa aga gag gaa gac aaa cca ttt aga gac tgt      1164
Leu Leu Lys Gly Gly Lys Arg Glu Glu Asp Lys Pro Phe Arg Asp Cys
270                 275                 280                 285
```

```
gca gat gta tat caa gct ggt ttt aat aaa agt gga atc tac act att    1212
Ala Asp Val Tyr Gln Ala Gly Phe Asn Lys Ser Gly Ile Tyr Thr Ile
            290                 295                 300 tat att aat aat atg cca gaa ccc aaa aag gtg ttt tgc aat atg gat    1260
Tyr Ile Asn Asn Met Pro Glu Pro Lys Lys Val Phe Cys Asn Met Asp
        305                 310                 315 gtc aat ggg gga ggt tgg act gta ata caa cat cgt gaa gat gga agt    1308
Val Asn Gly Gly Gly Trp Thr Val Ile Gln His Arg Glu Asp Gly Ser
    320                 325                 330 cta gat ttc caa aga ggc tgg aag gaa tat aaa atg ggt ttt gga aat    1356
Leu Asp Phe Gln Arg Gly Trp Lys Glu Tyr Lys Met Gly Phe Gly Asn
335                 340                 345 ccc tcc ggt gaa tat tgg ctg ggg aat gag ttt att ttt gcc att acc    1404
Pro Ser Gly Glu Tyr Trp Leu Gly Asn Glu Phe Ile Phe Ala Ile Thr
350                 355                 360                 365 agt cag agg cag tac atg cta aga att gag tta atg gac tgg gaa ggg    1452
Ser Gln Arg Gln Tyr Met Leu Arg Ile Glu Leu Met Asp Trp Glu Gly
            370                 375                 380 aac cga gcc tat tca cag tat gac aga ttc cac ata gga aat gaa aag    1500
Asn Arg Ala Tyr Ser Gln Tyr Asp Arg Phe His Ile Gly Asn Glu Lys
        385                 390                 395 caa aac tat agg ttg tat tta aaa ggt cac act ggg aca gca gga aaa    1548
Gln Asn Tyr Arg Leu Tyr Leu Lys Gly His Thr Gly Thr Ala Gly Lys
    400                 405                 410 cag agc agc ctg atc tta cac ggt gct gat ttc agc act aaa gat gct    1596
Gln Ser Ser Leu Ile Leu His Gly Ala Asp Phe Ser Thr Lys Asp Ala
415                 420                 425 gat aat gac aac tgt atg tgc aaa tgt gcc ctc atg tta aca gga gga    1644
Asp Asn Asp Asn Cys Met Cys Lys Cys Ala Leu Met Leu Thr Gly Gly
430                 435                 440                 445 tgg tgg ttt gat gct tgt ggc ccc tcc aat cta aat gga atg ttc tat    1692
Trp Trp Phe Asp Ala Cys Gly Pro Ser Asn Leu Asn Gly Met Phe Tyr
            450                 455                 460 act gcg gga caa aac cat gga aaa ctg aat ggg ata aag tgg cac tac    1740
Thr Ala Gly Gln Asn His Gly Lys Leu Asn Gly Ile Lys Trp His Tyr
        465                 470                 475 ttc aaa ggg ccc agt tac tcc tta cgt tcc aca act atg atg att cga    1788
Phe Lys Gly Pro Ser Tyr Ser Leu Arg Ser Thr Thr Met Met Ile Arg
    480                 485                 490 cct tta gat ttt tga aagcgcaatg tcagaagcga ttatgaaagc aacaagaaa    1843
Pro Leu Asp Phe
    495 tccggagaag ctgccaggtg agaaactgtt tgaaaacttc agaagcaaac aatattgtct    1903 cccttccagc aataagtggt agttatgtga agtcaccaag gttcttgacc gtgaatctgg    1963 agccgtttga gttcacaaga gtctctactt ggggtgacag tgctcacgtg gctcgactat    2023 agaaaactcc actgactgtc gggctttaaa aagggaagaa actgctgagc ttgctgtgct    2083 tcaaactact actggacctt attttggaac tatggtagcc agatgataaa tatggttaat    2143 ttc                                                                  2146

<210> SEQ ID NO 4
<211> LENGTH: 497
<212> TYPE: PRT
<213> ORGANISM: Artificial Sequence
<220> FEATURE:
<223> OTHER INFORMATION: Unknown Organism
```

-continued

```
<400> SEQUENCE: 4

Met Thr Val Phe Leu Ser Phe Ala Phe Leu Ala Ala Ile Leu Thr His
 1               5                  10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
             35                  40                  45

Glu His Asp Gly Asn Cys Arg Glu Ser Thr Thr Asp Gln Tyr Asn Thr
         50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Val Leu Leu Lys
            260                 265                 270

Gly Gly Lys Arg Glu Glu Asp Lys Pro Phe Arg Asp Cys Ala Asp Val
        275                 280                 285

Tyr Gln Ala Gly Phe Asn Lys Ser Gly Ile Tyr Thr Ile Tyr Ile Asn
    290                 295                 300

Asn Met Pro Glu Pro Lys Lys Val Phe Cys Asn Met Asp Val Asn Gly
305                 310                 315                 320

Gly Gly Trp Thr Val Ile Gln His Arg Glu Asp Gly Ser Leu Asp Phe
                325                 330                 335

Gln Arg Gly Trp Lys Glu Tyr Lys Met Gly Phe Gly Asn Pro Ser Gly
            340                 345                 350

Glu Tyr Trp Leu Gly Asn Glu Phe Ile Phe Ala Ile Thr Ser Gln Arg
        355                 360                 365

Gln Tyr Met Leu Arg Ile Glu Leu Met Asp Trp Glu Gly Asn Arg Ala
    370                 375                 380

Tyr Ser Gln Tyr Asp Arg Phe His Ile Gly Asn Glu Lys Gln Asn Tyr
385                 390                 395                 400

Arg Leu Tyr Leu Lys Gly His Thr Gly Thr Ala Gly Lys Gln Ser Ser
                405                 410                 415
```

```
Leu Ile Leu His Gly Ala Asp Phe Ser Thr Lys Asp Ala Asp Asn Asp
            420                 425                 430

Asn Cys Met Cys Lys Cys Ala Leu Met Leu Thr Gly Gly Trp Trp Phe
            435                 440                 445

Asp Ala Cys Gly Pro Ser Asn Leu Asn Gly Met Phe Tyr Thr Ala Gly
            450                 455                 460

Gln Asn His Gly Lys Leu Asn Gly Ile Lys Trp His Tyr Phe Lys Gly
465                 470                 475                 480

Pro Ser Tyr Ser Leu Arg Ser Thr Thr Met Met Ile Arg Pro Leu Asp
                485                 490                 495

Phe

<210> SEQ ID NO 5
<211> LENGTH: 2282
<212> TYPE: DNA
<213> ORGANISM: Artificial Sequence
<220> FEATURE:
<223> OTHER INFORMATION: Unknown Organism
<220> FEATURE:
<221> NAME/KEY: CDS
<222> LOCATION: (357)...(1847)

<400> SEQUENCE: 5
gaattcctgg gttggtgttt atctcctccc agccttgagg gagggaacaa cactgtagga      60
tctggggaga gaggaacaaa ggaccgtgaa agctgctctg taaaagctga cacagccctc     120
ccaagtgagc aggactgttc ttcccactgc aatctgacag tttactgcat gcctggagag     180
aacacagcag taaaaccag gtttgctact ggaaaagag gaaagagaag actttcattg      240
acggacccag ccatggcagc gtagcagccc tgcgtttcag acggcagcag ctcgggactc     300
tggacgtgtg tttgccctca gtttgctaa gctgctggtt tattactgaa gaaaga         356 atg tgg cag att gtt ttc ttt act ctg agc tgt gat ctt gtc ttg gcc      404
Met Trp Gln Ile Val Phe Phe Thr Leu Ser Cys Asp Leu Val Leu Ala
 1               5                  10                  15 gca gcc tat aac aac ttt cgg aag agc atg gac agc ata gga aag aag      452
Ala Ala Tyr Asn Asn Phe Arg Lys Ser Met Asp Ser Ile Gly Lys Lys
             20                  25                  30 caa tat cag gtc cag cat ggg tcc tgc agc tac act ttc ctc ctg cca      500
Gln Tyr Gln Val Gln His Gly Ser Cys Ser Tyr Thr Phe Leu Leu Pro
         35                  40                  45 gag atg gac aac tgc cgc tct tcc tcc agc ccc tac gtg tcc aat gct      548
Glu Met Asp Asn Cys Arg Ser Ser Ser Ser Pro Tyr Val Ser Asn Ala
     50                  55                  60 gtg cag agg gac gcg ccg ctc gaa tac gat gac tcg gtg cag agg ctg      596
Val Gln Arg Asp Ala Pro Leu Glu Tyr Asp Asp Ser Val Gln Arg Leu
 65                  70                  75                  80 caa gtg ctg gag aac atc atg gaa aac aac act cag tgg cta atg aag      644
Gln Val Leu Glu Asn Ile Met Glu Asn Asn Thr Gln Trp Leu Met Lys
                 85                  90                  95 ctt gag aat tat atc cag gac aac atg aag aaa gaa atg gta gag ata      692
Leu Glu Asn Tyr Ile Gln Asp Asn Met Lys Lys Glu Met Val Glu Ile
             100                 105                 110 cag cag aat gca gta cag aac cag acg gct gtg atg ata gaa ata ggg      740
Gln Gln Asn Ala Val Gln Asn Gln Thr Ala Val Met Ile Glu Ile Gly
         115                 120                 125 aca aac ctg ttg aac caa aca gct gag caa acg cgg aag tta act gat      788
Thr Asn Leu Leu Asn Gln Thr Ala Glu Gln Thr Arg Lys Leu Thr Asp
     130                 135                 140
```

```
gtg gaa gcc caa gta tta aat cag acc acg aga ctt gaa ctt cag ctc    836
Val Glu Ala Gln Val Leu Asn Gln Thr Thr Arg Leu Glu Leu Gln Leu
145                 150                 155                 160 ttg gaa cac tcc ctc tcg aca aac aaa ttg gaa aaa cag att ttg gac    884
Leu Glu His Ser Leu Ser Thr Asn Lys Leu Glu Lys Gln Ile Leu Asp
                165                 170                 175 cag acc agt gaa ata aac aaa ttg caa gat aag aac agt ttc cta gaa    932
Gln Thr Ser Glu Ile Asn Lys Leu Gln Asp Lys Asn Ser Phe Leu Glu
            180                 185                 190 aag aag gtg cta gct atg gaa gac aag cac atc atc caa cta cag tca    980
Lys Lys Val Leu Ala Met Glu Asp Lys His Ile Ile Gln Leu Gln Ser
        195                 200                 205 ata aaa gaa gag aaa gat cag cta cag gtg tta gta tcc aag caa aat   1028
Ile Lys Glu Glu Lys Asp Gln Leu Gln Val Leu Val Ser Lys Gln Asn
210                 215                 220 tcc atc att gaa gaa cta gaa aaa aaa ata gtg act gcc acg gtg aat   1076
Ser Ile Ile Glu Glu Leu Glu Lys Lys Ile Val Thr Ala Thr Val Asn
225                 230                 235                 240 aat tca gtt ctt caa aag cag caa cat gat ctc atg gag aca gtt aat   1124
Asn Ser Val Leu Gln Lys Gln Gln His Asp Leu Met Glu Thr Val Asn
                245                 250                 255 aac tta ctg act atg atg tcc aca tca aac tca gct aag gac ccc act   1172
Asn Leu Leu Thr Met Met Ser Thr Ser Asn Ser Ala Lys Asp Pro Thr
            260                 265                 270 gtt gct aaa gaa gaa caa atc agc ttc aga gac tgt gct gaa gta ttc   1220
Val Ala Lys Glu Glu Gln Ile Ser Phe Arg Asp Cys Ala Glu Val Phe
        275                 280                 285 aaa tca gga cac acc aca aat ggc atc tac acg tta aca ttc cct aat   1268
Lys Ser Gly His Thr Thr Asn Gly Ile Tyr Thr Leu Thr Phe Pro Asn
290                 295                 300 tct aca gaa gag atc aag gcc tac tgt gac atg gaa gct gga gga ggc   1316
Ser Thr Glu Glu Ile Lys Ala Tyr Cys Asp Met Glu Ala Gly Gly Gly
305                 310                 315                 320 ggg tgg aca att att cag cga cgt gag gat ggc agc gtt gat ttt cag   1364
Gly Trp Thr Ile Ile Gln Arg Arg Glu Asp Gly Ser Val Asp Phe Gln
                325                 330                 335 agg act tgg aaa gaa tat aaa gtg gga ttt ggt aac cct tca gga gaa   1412
Arg Thr Trp Lys Glu Tyr Lys Val Gly Phe Gly Asn Pro Ser Gly Glu
            340                 345                 350 tat tgg ctg gga aat gag ttt gtt tcg caa ctg act aat cag caa cgc   1460
Tyr Trp Leu Gly Asn Glu Phe Val Ser Gln Leu Thr Asn Gln Gln Arg
        355                 360                 365 tat gtg ctt aaa ata cac ctt aaa gac tgg gaa ggg aat gag gct tac   1508
Tyr Val Leu Lys Ile His Leu Lys Asp Trp Glu Gly Asn Glu Ala Tyr
370                 375                 380 tca ttg tat gaa cat ttc tat ctc tca agt gaa gaa ctc aat tat agg   1556
Ser Leu Tyr Glu His Phe Tyr Leu Ser Ser Glu Glu Leu Asn Tyr Arg
385                 390                 395                 400 att cac ctt aaa gga ctt aca ggg aca gcc ggc aaa ata agc agc atc   1604
Ile His Leu Lys Gly Leu Thr Gly Thr Ala Gly Lys Ile Ser Ser Ile
                405                 410                 415 agc caa cca gga aat gat ttt agc aca aag gat gga gac aac gac aaa   1652
Ser Gln Pro Gly Asn Asp Phe Ser Thr Lys Asp Gly Asp Asn Asp Lys
            420                 425                 430 tgt att tgc aaa tgt tca caa atg cta aca gga ggc tgg tgg ttt gat   1700
Cys Ile Cys Lys Cys Ser Gln Met Leu Thr Gly Gly Trp Trp Phe Asp
        435                 440                 445 gca tgt ggt cct tcc aac ttg aac gga atg tac tat cca cag agg cag   1748
Ala Cys Gly Pro Ser Asn Leu Asn Gly Met Tyr Tyr Pro Gln Arg Gln
450                 455                 460
```

```
aac aca aat aag ttc aac ggc att aaa tgg tac tac tgg aaa ggc tca    1796
Asn Thr Asn Lys Phe Asn Gly Ile Lys Trp Tyr Tyr Trp Lys Gly Ser
465                 470                 475                 480 ggc tat tcg ctc aag gcc aca acc atg atg atc cga cca gca gat ttc    1844
Gly Tyr Ser Leu Lys Ala Thr Thr Met Met Ile Arg Pro Ala Asp Phe
            485                 490                 495 taa acatcccagt ccacctgagg aactgtctcg aactattttc aaagacttaa         1897
gcccagtgca ctgaaagtca cggctgcgca ctgtgtcctc ttccaccaca gagggcgtgt  1957
gctcggtgct gacgggaccc acatgctcca gattagagcc tgtaaacttt atcacttaaa  2017
cttgcatcac ttaacggacc aaagcaagac cctaaacatc cataattgtg attagacaga  2077
acacctatgc aaagatgaac ccgaggctga gaatcagact gacagtttac agacgctgct  2137
gtcacaacca agaatgttat gtgcaagttt atcagtaaat aactggaaaa cagaacactt  2197
atgttataca atacagatca tcttggaact gcattcttct gagcactgtt tatacactgt  2257
gtaaataccc atatgtcctg aattc                                       2282

<210> SEQ ID NO 6
<211> LENGTH: 496
<212> TYPE: PRT
<213> ORGANISM: Artificial Sequence
<220> FEATURE:
<223> OTHER INFORMATION: Unknown Organism

<400> SEQUENCE: 6

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240
```

-continued

```
Asn Ser Val Leu Gln Lys Gln Gln His Asp Leu Met Glu Thr Val Asn
            245                 250                 255
Asn Leu Leu Thr Met Met Ser Thr Ser Asn Ser Ala Lys Asp Pro Thr
            260                 265                 270
Val Ala Lys Glu Glu Gln Ile Ser Phe Arg Asp Cys Ala Glu Val Phe
            275                 280                 285
Lys Ser Gly His Thr Thr Asn Gly Ile Tyr Thr Leu Thr Phe Pro Asn
    290                 295                 300
Ser Thr Glu Glu Ile Lys Ala Tyr Cys Asp Met Glu Ala Gly Gly Gly
305                 310                 315                 320
Gly Trp Thr Ile Ile Gln Arg Arg Glu Asp Gly Ser Val Asp Phe Gln
                325                 330                 335
Arg Thr Trp Lys Glu Tyr Lys Val Gly Phe Gly Asn Pro Ser Gly Glu
                340                 345                 350
Tyr Trp Leu Gly Asn Glu Phe Val Ser Gln Leu Thr Asn Gln Gln Arg
                355                 360                 365
Tyr Val Leu Lys Ile His Leu Lys Asp Trp Glu Gly Asn Glu Ala Tyr
    370                 375                 380
Ser Leu Tyr Glu His Phe Tyr Leu Ser Ser Glu Glu Leu Asn Tyr Arg
385                 390                 395                 400
Ile His Leu Lys Gly Leu Thr Gly Thr Ala Gly Lys Ile Ser Ser Ile
                405                 410                 415
Ser Gln Pro Gly Asn Asp Phe Ser Thr Lys Asp Gly Asp Asn Asp Lys
                420                 425                 430
Cys Ile Cys Lys Cys Ser Gln Met Leu Thr Gly Gly Trp Trp Phe Asp
                435                 440                 445
Ala Cys Gly Pro Ser Asn Leu Asn Gly Met Tyr Tyr Pro Gln Arg Gln
    450                 455                 460
Asn Thr Asn Lys Phe Asn Gly Ile Lys Trp Tyr Tyr Trp Lys Gly Ser
465                 470                 475                 480
Gly Tyr Ser Leu Lys Ala Thr Thr Met Met Ile Arg Pro Ala Asp Phe
                485                 490                 495
```